(12) United States Patent
Davioud-Charvet et al.

(10) Patent No.: US 7,923,434 B2
(45) Date of Patent: Apr. 12, 2011

(54) PHOSPHOLE DERIVATIVES COMPLEXED WITH METALS, AND PHARMACEUTICAL USES THEREOF

(75) Inventors: Elisabeth Davioud-Charvet, Perenchies (FR); Katja Becker-Brandenburg, Dutenhofen (DE); Valérie Deborde, Iffendic (FR); Régis Reau, Des Fougeretz (FR); R. Heiner Schirmer, Heidelberg (DE); Christel Herold-Mende, Bammental (DE)

(73) Assignee: Centre National de la Recherche Scientifique, Paris (FR)

( * ) Notice: Subject to any disclaimer, the term of this patent is extended or adjusted under 35 U.S.C. 154(b) by 808 days.

(21) Appl. No.: 11/658,694

(22) PCT Filed: Jul. 29, 2005

(86) PCT No.: PCT/FR2005/002004
§ 371 (c)(1),
(2), (4) Date: Apr. 6, 2007

(87) PCT Pub. No.: WO2006/024770
PCT Pub. Date: Mar. 9, 2006

(65) Prior Publication Data
US 2008/0045465 A1    Feb. 21, 2008

(30) Foreign Application Priority Data

Jul. 30, 2004   (FR) ..................... 04 08427

(51) Int. Cl.
*C07F 1/12*    (2006.01)
*C07F 15/00*   (2006.01)
*C07H 23/00*   (2006.01)
*A61K 31/70*   (2006.01)
*A61P 35/00*   (2006.01)

(52) U.S. Cl. .............. 514/24; 536/17.1; 546/2
(58) Field of Classification Search ........................ None
See application file for complete search history.

(56) References Cited

FOREIGN PATENT DOCUMENTS
WO    WO 01/77121    10/2001

OTHER PUBLICATIONS

Hay, Caroline et al., Chemical Communications, "2,5-Di(2-pyridyl)phospholes: model compounds for the engineering of pi-conjugated donor-acceptor co-oligomers with a chemically tunable HOMO-LUMO gap", (1999), pp. 345-346.*

Hay, Caroline et al., Chemistry, a European Journal, "Phosphole-Containing Pi-Conjugated Systems: From Model Molecules to Polymer Films on Electrodes" (2001), vol. 7, issue 19, pp. 4222-4236.*

Tetrahydrofuran available at http://www.lyondellbasell.com/Products/ByCategory/basic-chemicals/PerformanceChemicalsAndSolvents/Tetrahydrofuran/ ( last viewed Nov. 4, 2009).*

Remington, The Science and Practice of Pharmacy, 20th edition, copyright 2000, chapter 16, pp. 218-220.*

Deponte M et al:. "Mechanistic Studies on a Novel, Highly Potent Gold-Phosphole Inhibitor of Human Glutathione Reductase", Journal of Biological Chemistry, American Society of Biolchemical Biologists, Birmingham, US vol. 280, No. 21, May 27, 2005, pp. 20628-20637, XP008059661, ISSN: 0021-9258 Le Document En Entier.

Hay C et al:, "A Bridging Ligand Featuring Terminal 2-Pyridylphosphole Moieties: Synthesis, Optical Poroperties and Ru(II)-Complex", Journal of Organometallic Chemistry, Elsevier-Sequoia S.A. Lausanne, Ch, vol. 643-644, Feb. 1, 2002, pp. 494-497, XP004339612, ISSN: 0022-328X, Le Document En Entier.

Sautthier M et al:, "A Rare Phosphane Coordination Mode: A Symmetrically MU2-Bridging Phosphole in a Dinuclear Palladium(I) Complex", Angewandte Chemie. International Edition, Verlag, Chemie. Weinheim, DE, vol. 40 No. 1, J Javier 2001 (Jan. 5, 2001), pp. 228-231, XP002223439, ISSN: 0570-0833, Le Document En Entier.

Leca, Francois et al:, "Stereospecific Isomerization of P-Heterocycles Triggered by Coordinationi Synthesis of the First P, N-Chelates Featuring A 2-Phospholene Moiety", Chemical Communications (Cambridge, United Kingdom), (14), 1774-1775 Coden: CHCOFS; ISSN: 1359-7345, 2003, XP008044152, Le Document En Entier.

Sauthier M et al:, "Palladium Complexes of a Novel Family of P,N-Chelates, The 2-(2-Pyridyl) Phospholes: Synthesis, Structural Characterization and Catalytic Activity for Olefin/Co Copolymerization", Organometallics, ACS, Washington, DC, US, vol. 21, No. 8, Apr. 15, 2002, pp. 1591-1602, XP001103869 ISSN: 0276-7333 Cite Dans la Demande le Document En Entier.

* cited by examiner

*Primary Examiner* — Shaojia Anna Jiang
*Assistant Examiner* — Bahar Schmidtmann
(74) *Attorney, Agent, or Firm* — Young & Thompson

(57) ABSTRACT

The invention concerns pharmaceutical compositions comprising as active compound at least one compound of general formula (A), wherein: M represents a metal atom, and their uses in particular for preventing or treating pathologies associated with an excess activity of glutathion reductase and/or thioredoxin reductase.

26 Claims, 1 Drawing Sheet

PHOSPHOLE DERIVATIVES COMPLEXED WITH METALS, AND PHARMACEUTICAL USES THEREOF

Figure 1:
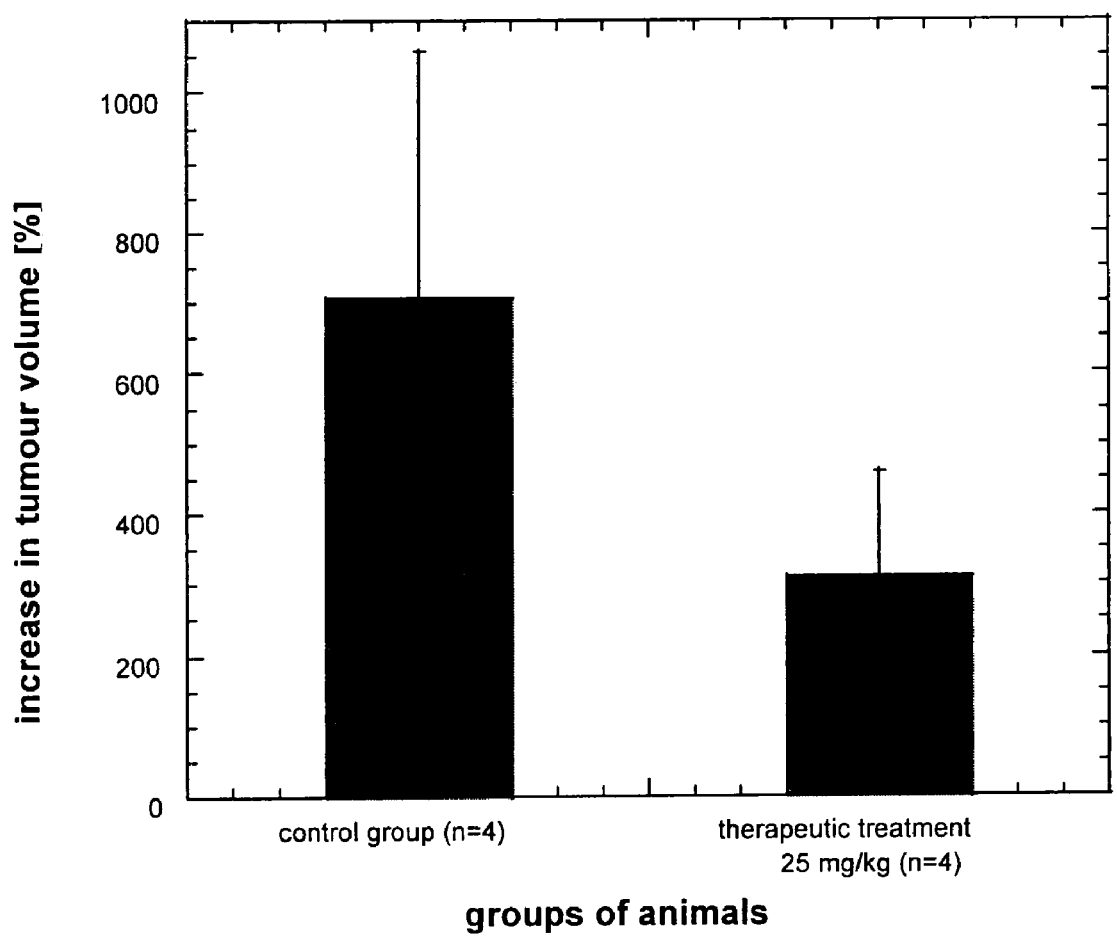

A subject of the present invention is pharmaceutical compositions comprising phosphole derivatives complexed with metals, and their uses for the preparation of medicaments intended for the prevention or treatment of pathologies linked to excessive glutathione reductase and/or thioredoxin reductase activity.

The thioredoxin reductases (TrxR) like the glutathione reductases (GR) are NADPH-dependent dimeric flavoenzymes having in their catalytic site a redox-active centre. TrxR reduces oxidized thioredoxin (Trx), a 12 kDa disulphide protein, to thioredoxin dithiol; GR reduces glutathione disulphide to reduced glutathione (GSH) (Williams, 1992; Holmgren, 2000). Trx and GSH in reduced form play an essential role in cell redox regulation, antioxidizing defence, enzymatic regulation, apoptosis and cell proliferation associated with tumours. The systems based on glutathione and thioredoxin provide the reductive equivalents for a large number of intra- and extra-cellular processes including the reduction of ribonucleic acids, the reduction of compounds of low molecular weight such as lipoamide, lipoic acid, hydrogen peroxide, the lipid hydroperoxides, S-nitrosoglutathione, ascorbate, alloxane, ebselen (diselenide), methylseleninate, ubiquinone and proteins such as those binding to calcium (proteins 1 and 2), NK-lysine, the protein disulphide isomerase, and the glutathione peroxidases (Arner & Holmgren, 2000; Holmgren, 2000; Gromer & Gross, 2002; May et al., 2002; Zhong & Holmgren, 2002; Zhao et al., 2002; Zhao & Holmgren, 2002; Xia et al., 2003). Moreover, the Trx's and/or the GSH modulate the activity of the transcription factors such as NF-Y, Pax-8, TTF-1, NF-κB, and serve as an activation factor of the glucocorticoid receptor, play a role in the biosynthesis of the proteins, have an impact on the structure of the export proteins, regulate the activity of the enzymes, serve as antioxidants and can act in an extracellular manner as an autocrine growth factor (Holmgren, 2000).

From the point of view of catalytic mechanism, the electrons are transferred from the NADPH to the flavin adenine dinucleotide (FAD), the prosthetic group of these enzymes, and from there to the disulphide bridge of the active site (Cys58 and Cys63 in human GR). In the GRs, the electrons are then transferred from the dithiol, generated during catalysis, to the substrate glutathione disulphide. However, in the TrxRs of mammals, an additional redox centre, represented by a cysteine-selenocysteine pair located in the C-terminal part transfers the reductive equivalents from the first active site in the N-terminal part to the second active site in the C-terminal part. The flexibility of this C-terminal polypeptide chain allows the exposure of the reductive equivalents at the surface of the protein, allowing the reduction of the Trx, but also of a large spectrum of different substrates (Gladyshev et al., 1996; Arscott et al., 1997; Gromer et al., 1997 & 1998; Tamura & Stadtman, 1996; Zhong et al., 1998 & 2000). Different approaches have demonstrated that the selenocysteine is located on an extremely flexible accessible arm of the protein and is essential for the catalytic mechanism. The first three-dimensional structure of a mammalian TrxR—the only one described up to now—was resolved by Sandalova et al., 2001. The overall structure of the mutant TrxR of rat studied, SeCys498Cys, is similar to GR at the level of the domains linking the FAD and the NADPH. The 3D structure of human GR is well known.

Trx is secreted by normal and neoplastic cells. It acts in the reduced form as an autocrine growth factor (Powis et al., 1998). Numerous tumour cells are known to express increased levels of Trx, glutathione, and two reductases TrxR and GR (Kahlos et. al., 2001; Soini et al., 2001). The involvement of the thioredoxin/TrxR system in oncogenesis and in tumorogenesis and its potential targeting in anticancer chemotherapy were recently confirmed by Lincoln et al., 2003. The mitochondrial TrxR was demonstrated to participate in the regulation of cell proliferation (Kim et al., 2003) and Trx-1 regulates the expression of the genes specific to breast cancer (Husbeck & Powis, 2002). The overexpression of Trx-1 results in an increase in the production of the vascular endothelial growth factor, and in angiogenesis at the level of the tumour (Welsh et al., 2002). Moreover, since human TrxR is inhibited by a variety of anticancer active ingredients (such as cisPlatin, doxorubicin, nitrosourea BCNU etc.), the enzyme is generally recognized to promote cell viability and multiplication. Moreover, the GRs and TrxRs play a crucial role in the mechanisms of resistance to medicaments.

The wide functional spectrum of mammalian TrxRs and GRs, their involvement in a variety of cell processes and therefore their potential importance in a multitude of diseases make these two flavoenzymes extremely useful as potential candidates for the development of medicaments against tumours, parasites, and rheumatoid inflammatory diseases (Sarma et al., 2003). A specific inactivation of these disulphide reductases is in reality an approach attempting, simultaneously, to reduce the synthesis of DNA, the antioxidizing defence, the stimulation of autocrine growth, and the growth of tumour cells. A number of medicaments used clinically and experimentally were recently demonstrated to effectively inhibit the disulphide reductases. A prime example is the inhibition of GR and TrxR by the cytostatic agent BCNU (carmustine). More usefully, BCNU is one of the rare cytostatic agents used successfully in the treatment of glioblastomas. GR is inhibited by isoalloxazine derivatives, dimerization inhibitors, naphthoquinone derivatives (Davioud-Charvet et al., 2001), and a variety of compounds releasing nitric oxide (Becker et al., 1998 & 2000; Savvides et al., 2002). Different compounds were described as inhibiting human TrxR and having antitumour effects; these compounds include gold complexes (I) such as aurothioglucose and auranofin (Gromer et al., 1998; Smith et al., 1999), trivalent arsenical derivatives such as methyl-As(III) (Lin et al., 2001), water-soluble organotellurium compounds, and also naphthoquinones (Wipf et al., 2001; Imler et al., 2002; Engman et al., 2003), and the complexes of cis-diaminedichloroplatinum (II) (Arner et al., 2001). Moreover, the complexes of (2.2':6', 2'-terpyridine) platinum (II) were described as quasi-stoichiometrically targeting human TrxR, which is effectively inhibited in vitro. In vivo, the proliferation of different glioblastoma cell lines is efficiently inhibited by these compounds (Becker et al., 2001; Ross et al., 2000).

Mannich bases also represent TrxR inhibitors of interest (Davioud-Charvet et al., 2003) as these compounds have been described and developed as potential antineoplastic agents for the last 15 years (Dimmock et al., 1998). Considering all this data, the inhibitors of GRs and TrxRs are very useful as potential cytostatic and anti-rheumatism medicaments and are excellent tools for studying the function of the cell networks regulated in a redox manner.

The present invention results from the demonstration of the fact that phosphole derivatives containing gold and platinum, the synthesis of which has already been described (phosphole synthesis: Hay et al., 2001; Sauthier et al., 2002; synthesis of platinum complexes: Fave C., 2003; synthesis of gold complexes: Nelsen L., 2002), or which had never been synthesized previously, are powerful inhibitors of human GR and TrxR (see Table 1 hereafter), inhibit the growth of tumour cell lines (see Table 2 below) and are active in vivo against tumours in rats. Moreover, the Inventors have shown that the above phosphole derivatives, not complexed with metals, also had an activity of inhibition of the growth of tumour cell lines (see Table 2 below).

Thus the essential purpose of the present invention is to provide novel pharmaceutical compositions for the prevention or treatment of pathologies in particular linked to excessive glutathione reductase and/or thioredoxin reductase activity.

A subject of the present invention is a pharmaceutical composition, characterized in that it comprises as active ingredient at least one compound of general formula (A) below:

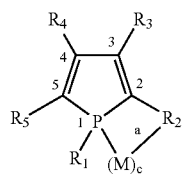

(A)

in which:
a represents a single bond or no bond,
c represents 0 when M is absent or 1 when M is present,
$R_1$ represents a
  linear or branched alkyl group with 1 to 6 carbon atoms,
  saturated or unsaturated cycloalkyl group with 3 to 7 carbon atoms,
  aryl group with 6 to 14 carbon atoms,
  linear or branched alkoxy group with 1 to 6 carbon atoms,
  saturated or unsaturated cycloalkoxy group with 3 to 7 carbon atoms,
  aryloxy group with 6 to 14 carbon atoms,
  linear or branched alkylthio group with 1 to 6 carbon atoms,
  saturated or unsaturated cycloalkylthio group with 3 to 7 carbon atoms, or
  arylthio group with 6 to 14 carbon atoms,
optionally substituted by one or more groups, identical or different, chosen from a halogen atom, in particular F, Cl, Br, or I, in particular F, a linear or branched alkyl group with 1 to 6 carbon atoms, optionally substituted by one or more halogen atoms, such as the $CF_3$ group, or an aryl group with 6 to 14 carbon atoms;
$R_2$ represents a nitrogen-containing heteroaryl group or a nitrogen-containing heterocycle with 5 or 6 atoms having from 1 to 4 nitrogen atoms;
$R_3$ and $R_4$ represent, independently of one another, a hydrogen atom, or a
  linear or branched alkyl group with 1 to 6 carbon atoms,
  saturated or unsaturated cycloalkyl group with 3 to 7 carbon atoms,
  aryl group with 6 to 14 carbon atoms,
  linear or branched alkoxy group with 1 to 6 carbon atoms,
  saturated or unsaturated cycloalkoxy group with 3 to 7 carbon atoms,
  aryloxy group with 6 to 14 carbon atoms,
  linear or branched alkylthio group with 1 to 6 carbon atoms,
  saturated or unsaturated cycloalkylthio group with 3 to 7 carbon atoms, or
  arylthio group with 6 to 14 carbon atoms,
optionally substituted by one or more groups, identical or different, chosen from a halogen atom, in particular F, Cl, Br, or I, in particular F, a linear or branched alkyl group with 1 to 6 carbon atoms, optionally substituted by one or more halogen atoms, in particular $CF_3$, or an aryl group with 6 to 14 carbon atoms, if appropriate an alkyl group can bridge the carbon atoms in positions 3 and 4 of the phosphole ring carrying, respectively, the substituents $R_3$ and $R_4$, so as to form a ring with 3 to 8 carbon atoms;
$R_5$ represents a hydrogen atom, a heterocycle with five or six members having from 1 to 4 nitrogen or sulphur atoms, or a
  linear or branched alkyl group with 1 to 6 carbon atoms,
  saturated or unsaturated cycloalkyl group with 3 to 7 carbon atoms,
  aryl group with 6 to 14 carbon atoms,
  linear or branched alkoxy group with 1 to 6 carbon atoms,
  saturated or unsaturated cycloalkoxy group with 3 to 7 carbon atoms,
  aryloxy group with 6 to 14 carbon atoms,
  linear or branched alkylthio group with 1 to 6 carbon atoms,
  saturated or unsaturated cycloalkylthio group with 3 to 7 carbon atoms, or
  arylthio group with 6 to 14 carbon atoms,
optionally substituted by one or more groups, identical or different, chosen from a halogen atom, in particular F, Cl, Br, or I, in particular F, a linear or branched alkyl group with 1 to 6 carbon atoms, optionally substituted by one or more halogen atoms, in particular $CF_3$, or an aryl group with 6 to 14 carbon atoms;
if appropriate (c=1) M represents a metal atom, optionally carrying from 1 to 2 substituents, $R_6$ and $R_7$, identical or different, which substituents are chosen from
  a halogen atom,
  a thio-osidic group with 3 to 60 carbon atoms, optionally substituted by one or more groups, identical or different, chosen from the protective groups of hydroxyl and amine groups, such as an alkanoyl group with 2 to 6 carbon atoms, or an arylcarbonyl group with 6 to 14 carbon atoms,
  a peptide group comprising from 1 to 5 amino acids, at least one of the amino acids comprising a thio group, such as S-cysteine or S-glutathione, or
  a linear or branched thioalkyl group with 1 to 6 carbon atoms, a saturated or unsaturated thiocycloalkyl group with 3 to 7 carbon atoms or a thioaryl or thioheteroaryl group with 6 to 14 carbon atoms, such as a thiophenyl, 2-thiopyridyl or 4-thiopyridyl group, optionally substituted by one or more groups, identical or different, chosen from a halogen atom, in particular F, Cl, Br or I, in particular F, an alkyl group with 1 to 6 carbon atoms, optionally substituted by one or more halogen atoms, in particular $CF_3$, or an aryl group with 6 to 14 carbon atoms;
in combination with a pharmaceutically acceptable vehicle.

In a particular embodiment of the invention, in the compound of formula (A) above, the metal atom M is different from palladium (Pd), in particular when $R_6$ and/or $R_7$ represent a halogen atom. In fact, the significant reactivity of the palladium can be responsible for undesirable effects in a patient to whom a compound of formula (A) is administered.

By "thio-osidic group" is meant a group comprising at least one monosaccharide, said monosaccharide comprising at least one thio group, in particular replacing at least one hydroxyl group of said monosaccharide, and optionally one or more amine groups. More particularly, and if appropriate, the thio group replaces the hydroxyl group of the hemiacetalic function of the monosaccharide in the cyclic form. The osidic group according to the invention can in particular comprise from 1 to 10 monosaccharides, at least one of which is a thio-monosaccharide.

According to the invention the thio-osidic group can in particular represent: thioglucose, thiomannose, thiogalactose, thioribose, thioxylose, thio-allose, thiotalose, thiofucose, thio-N-acetyl-glucosamine, thio-N-acetyl-galactosamine, thio-N-acetyl mannosamine, or thiolactose.

According to the invention, the protective groups of hydroxyl and amine groups represent in particular: an acetyl group, a propionate group, a butyrate group, or a benzoyl group.

A subject of the present invention is also a pharmaceutical composition as defined above, characterized in that it comprises as active ingredient at least one compound of general formula (I) below:

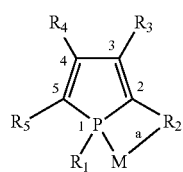

(I)

in which:
a represents a single bond or no bond,
$R^1$ represents a
  linear or branched alkyl group with 1 to 6 carbon atoms,
  saturated or unsaturated cycloalkyl group with 3 to 7 carbon atoms,
  aryl group with 6 to 14 carbon atoms,
  linear or branched alkoxy group with 1 to 6 carbon atoms,
  saturated or unsaturated cycloalkoxy group with 3 to 7 carbon atoms,
  aryloxy group with 6 to 14 carbon atoms,
  linear or branched alkylthio group with 1 to 6 carbon atoms,
  saturated or unsaturated cycloalkylthio group with 3 to 7 carbon atoms, or
  arylthio group with 6 to 14 carbon atoms,
optionally substituted by one or more groups, identical or different, chosen from a halogen atom, in particular F, Cl, Br, or I, in particular F, a linear or branched alkyl group with 1 to 6 carbon atoms, optionally substituted by one or more halogen atoms, in particular $CF_3$, or an aryl group with 6 to 14 carbon atoms;
  $R_2$ represents a nitrogen-containing heteroaryl group or a nitrogen-containing heterocycle with 5 or 6 atoms having from 1 to 4 nitrogen atoms;
  $R_3$ and $R_4$ represent, independently of one another, a hydrogen atom, or a
    linear or branched alkyl group with 1 to 6 carbon atoms,
    saturated or unsaturated cycloalkyl group with 3 to 7 carbon atoms,
    aryl group with 6 to 14 carbon atoms,
    linear or branched alkoxy group with 1 to 6 carbon atoms,
    saturated or unsaturated cycloalkoxy group with 3 to 7 carbon atoms,
    aryloxy group with 6 to 14 carbon atoms,
    linear or branched alkylthio group with 1 to 6 carbon atoms,
    saturated or unsaturated cycloalkylthio group with 3 to 7 carbon atoms, or
    arylthio group with 6 to 14 carbon atoms,
  optionally substituted by one or more groups, identical or different, chosen from a halogen atom, in particular F, Cl, Br, or I, in particular F, a linear or branched alkyl group with 1 to 6 carbon atoms, optionally substituted by one or more halogen atoms, in particular $CF_3$, or an aryl group with 6 to 14 carbon atoms, if appropriate an alkyl group can bridge the carbon atoms in positions 3 and 4 of the phosphole ring carrying, respectively, the substituents $R_3$ and $R_4$, so as to form a ring with 3 to 8 carbon atoms;
  $R_5$ represents a hydrogen atom, a heterocycle with five or six members having from 1 to 4 nitrogen or sulphur atoms, or a
    linear or branched alkyl group with 1 to 6 carbon atoms,
    saturated or unsaturated cycloalkyl group with 3 to 7 carbon atoms,
    aryl group with 6 to 14 carbon atoms,
    linear or branched alkoxy group with 1 to 6 carbon atoms,
    saturated or unsaturated cycloalkoxy group with 3 to 7 carbon atoms,
    aryloxy group with 6 to 14 carbon atoms,
    linear or branched alkylthio group with 1 to 6 carbon atoms,
    saturated or unsaturated cycloalkylthio group with 3 to 7 carbon atoms, or
    arylthio group with 6 to 14 carbon atoms,
  optionally substituted by one or more groups, identical or different, chosen from a halogen atom, in particular F, Cl, Br, or I, in particular F, a linear or branched alkyl group with 1 to 6 carbon atoms, optionally substituted by one or more halogen atoms, in particular $CF_3$, or an aryl group with 6 to 14 carbon atoms;
  M represents a metal atom, optionally carrying from 1 to 2 substituents, $R_6$ and $R_7$, identical or different, which substituents are chosen from
    a halogen atom,
    a thio-osidic group with 3 to 60 carbon atoms, optionally substituted by one or more groups, identical or different, chosen from the protective groups of hydroxyl and amine groups, such as an alkanoyl group with 2 to 6 carbon atoms, or an arylcarbonyl group with 6 to 14 carbon atoms,
    a peptide group comprising from 1 to 5 amino acids, at least one of the amino acids comprising a thio group, such as S-cysteine or S-glutathione, or
    a linear or branched thioalkyl group with 1 to 6 carbon atoms, a saturated or unsaturated thiocycloalkyl group with 3 to 7 carbon atoms or a thioaryl or thioheteroaryl group with 6 to 14 carbon atoms, such as a thiophenyl, 2-thiopyridyl or 4-thiopyridyl group, optionally substituted by one or more groups, identical or different, chosen from a halogen atom, in particular F, Cl, Br or I, in particular F, an alkyl group with 1 to 6 carbon atoms, optionally substituted by one or more halogen atoms, in particular $CF_3$, or an aryl group with 6 to 14 carbon atoms;

in combination with a pharmaceutically acceptable vehicle.

The invention relates more particularly to a pharmaceutical composition as defined above, characterized in that it comprises as active ingredient at least one compound of general formula (II) below:

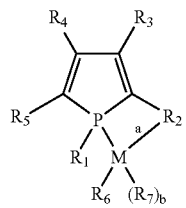

(II)

in which:

a represents a single bond or no bond, b represents 0 or 1, $R_1$, $R_2$, $R_3$, $R_4$ and $R_5$ are as defined above, $R_6$ and $R_7$ represent, independently of one another,

- a halogen atom,
- a thio-osidic group with 3 to 60 carbon atoms, optionally substituted by one or more groups, identical or different, chosen from the protective groups of hydroxyl and amine groups, such as an alkanoyl group with 2 to 6 carbon atoms, or an arylcarbonyl group with 6 to 14 carbon atoms,
- a peptide group comprising from 1 to 5 amino acids, at least one of the amino acids comprising a thio group, such as S-cysteine or S-glutathione, or
- a linear or branched thioalkyl group with 1 to 6 carbon atoms, a saturated or unsaturated thiocycloalkyl group with 3 to 7 carbon atoms or a thioaryl or thioheteroaryl group with 6 to 14 carbon atoms, such as a thiophenyl, 2-thiopyridyl or 4-thiopyridyl group, optionally substituted by one or more groups, identical or different, chosen from a halogen atom, in particular F, Cl, Br or I, in particular F, an alkyl group with 1 to 6 carbon atoms, optionally substituted by one or more halogen atoms, in particular $CF_3$, or an aryl group with 6 to 14 carbon atoms;

M represents a divalent, trivalent or tetravalent metal atom, providing that when M represents a divalent metal atom then a represents no bond and b is 0, when M represents a trivalent metal atom then a represents no bond and b is 1 and when M represents a tetravalent metal atom then a represents a single bond and b is 1;

in combination with a pharmaceutically acceptable vehicle.

In a preferred embodiment of the invention, in the compounds of formula (A), (I) or (II) above, M is chosen, if appropriate, from Ag, Cu, Mn, Au and Pt, and in particular from Au and Pt A more particular subject of the invention is a pharmaceutical composition comprising at least one compound of formula (I) or (II) as defined above, characterized in that it comprises as active ingredient at least one compound of general formula (III):

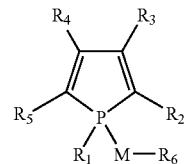

(III)

in which $R_1$, $R_2$, $R_3$, $R_4$, $R_5$ and $R_6$ are as defined above, and M represents a divalent metal atom, such as Au, in combination with a pharmaceutically acceptable vehicle.

A pharmaceutical composition comprising at least one compound of formula (III) as defined above as particularly preferred, is characterized in that it comprises as active ingredient at least one compound of general formula (IV) below:

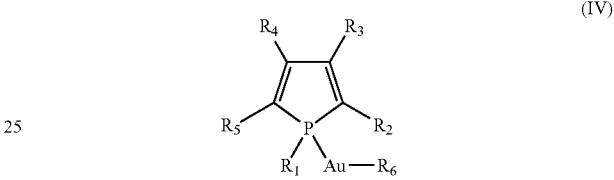

(IV)

in particular at least one compound of general formula (IV') below:

(IV')

in which, $R_2$, $R_3$, $R_4$, $R_5$ and $R_6$ are as defined above, in combination with a pharmaceutically acceptable vehicle.

The invention also relates to a pharmaceutical composition comprising at least one compound of formula (I) or (II) as defined above, characterized in that it comprises as active ingredient at least one compound of general formula (V):

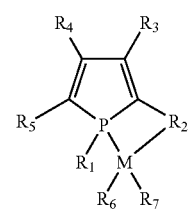

(V)

in which $R_1$, $R_2$, $R_3$, $R_4$, $R_5$, $R_6$ and $R_7$ are as defined above, and M represents a tetravalent metal atom, such as Pt, in combination with a pharmaceutically acceptable vehicle.

A pharmaceutical composition comprising at least one compound of formula (V) as defined above as particularly preferred, is characterized in that it comprises as active ingredient at least one compound of general formula (VI) below:

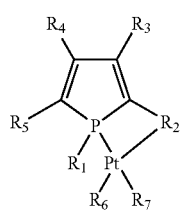

(VI)

in particular at least one compound of general formula (VI') below:

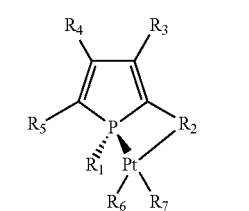

(VI')

in which $R_1$, $R_2$, $R_3$, $R_4$, $R_5$, $R_6$ and $R_7$ are as defined above,
in combination with a pharmaceutically acceptable vehicle.

A more particular subject of the invention is a pharmaceutical composition comprising at least one compound of formula (VI) as defined above, characterized in that it comprises as active ingredient at least one compound of general formula (VII) below:

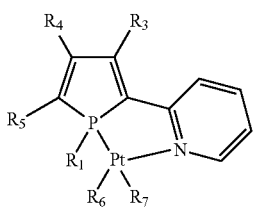

(VII)

in particular at least one compound of general formula (VII') below:

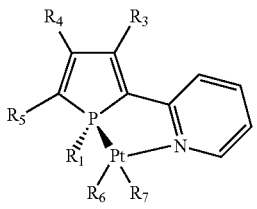

(VII')

in which $R_1$, $R_3$, $R_4$, $R_5$, $R_6$ and $R_7$ are as defined above,
in combination with a pharmaceutically acceptable vehicle.

A subject of the invention is also any pharmaceutical composition as defined above, characterized in that:
$R_1$ represents a cycloalkyl group with 3 to 7 carbon atoms or an aryl group with 6 to 14 carbon atoms, and more particularly a cyclohexyl or phenyl group;
$R_2$ represents a nitrogen-containing heteroaryl group with six atoms having from 1 to 3 nitrogen atoms, and more particularly the 2-pyridyl group;
$R_3$ and $R_4$ represent independently of one another an alkyl group with 1 to 6 carbon atoms, and more particularly an alkyl group with 3 or 4 carbon atoms linking the atoms in positions 3 and 4 of the phosphole ring;
$R_5$ represents an aryl group with 6 to 14 carbon atoms, a thienyl group with 6 to 14 carbon atoms, or a pyridyl group with 6 to 14 carbon atoms, substituted or non-substituted, and more particularly a phenyl, 2-thienyl or 2-pyridyl group;
$R_6$ and if appropriate $R_7$ represent independently of one another a halogen, and more particularly a chlorine atom, a thio-monosaccharide, in particular chosen from a thiopentose or a thiohexose, or a thiodioside, optionally substituted by one or more protective groups of the hydroxyl or amine groups, and more particularly thioglucose, thioglucose tetraacetate, thiomannose, thiomannose tetraacetate, thiogalactose, thiogalactose tetraacetate, thioribose, thioribose triacetate, thioxylose, thioxylose triacetate, thio-allose, thio-allose tetraacetate, thiotalose, thiotalose tetraacetate, thiofucose, thiofucose tetraacetate, thio-N-acetyl-glucosamine, thio-N-acetyl-glucosamine triacetate, thio-N-acetyl-galactosamine, thio-N-acetyl-galactosamine triacetate, thio-N-acetyl mannosamine, thio-N-acetyl mannosamine triacetate, thiolactose, thiolactose hepta-acetate.

A more particular subject of the invention is a pharmaceutical composition as defined above, characterized in that it comprises as active ingredient at least one compound of the following formula:

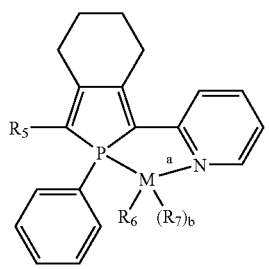

in which $R_5$ represents a 2-thienyl or 2-pyridyl group, M represents Au or Pt, a represents a single bond when M represents Pt or no bond when M represents Au, b represents 1 when M represents Pt and 0 when M represents Au, and $R_6$ and $R_7$ are as defined above.

The invention relates more particularly to a pharmaceutical composition as defined above, characterized in that it comprises as active ingredient at least one compound of the following formula:

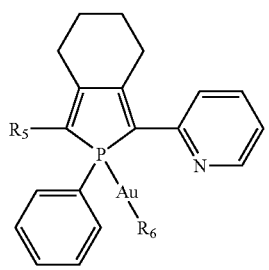

in which R₅ represents a 2-thienyl or 2-pyridyl group and R₆ is as defined above.

A more particular subject of the invention is any pharmaceutical composition as defined above, characterized in that it comprises as active ingredient at least one compound of formula (1), (2), (3), (4), or (8) below:

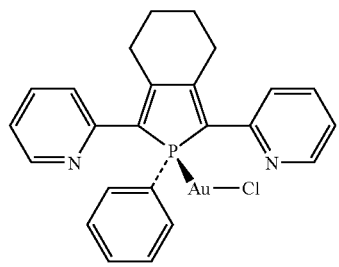
(1)

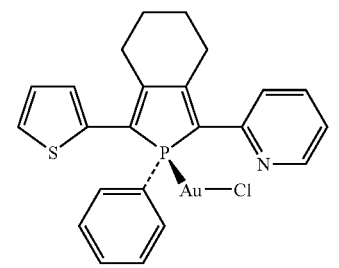
(2)

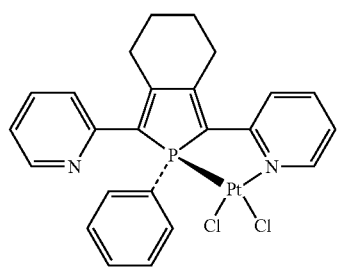
(3)

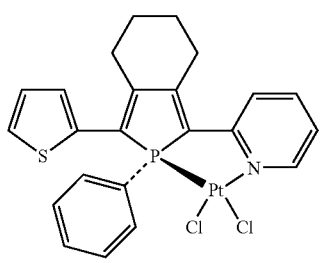
(4)

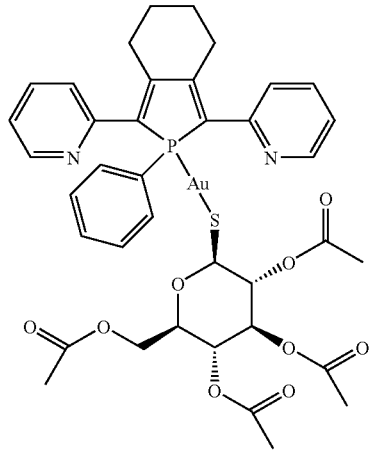
(8)

The present invention also relates to a pharmaceutical composition as defined above, characterized in that it comprises as active ingredient at least one compound of general formula (A) corresponding in particular to general formula (VIII) below:

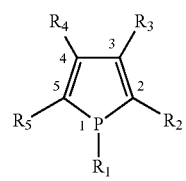
(VIII)

in which:
R₁ represents a
  linear or branched alkyl group with 1 to 6 carbon atoms,
  saturated or unsaturated cycloalkyl group with 3 to 7 carbon atoms,
  aryl group with 6 to 14 carbon atoms,
  linear or branched alkoxy group with 1 to 6 carbon atoms,
  saturated or unsaturated cycloalkoxy group with 3 to 7 carbon atoms,
  aryloxy group with 6 to 14 carbon atoms,
  linear or branched alkylthio group with 1 to 6 carbon atoms,
  saturated or unsaturated cycloalkylthio group with 3 to 7 carbon atoms, or
  arylthio group with 6 to 14 carbon atoms,
    optionally substituted by one or more groups, identical or different, chosen from a halogen atom, in particular F, Cl, Br or I, in particular F, an alkyl group with 1 to 6 carbon atoms, optionally substituted by one or more halogen atoms, in particular CF₃, or an aryl group with 6 to 14 carbon atoms;

R₂ represents a nitrogen-containing heteroaryl group or a nitrogen-containing heterocycle with 5 or 6 atoms having from 1 to 4 nitrogen atoms;

R₃ and R₄ represent, independently of one another, a
hydrogen atom, or a
linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms, optionally substituted by one or more groups, identical or different, chosen from a halogen atom, in particular F, Cl, Br or I, in particular F, an alkyl group with 1 to 6 carbon atoms, optionally substituted by one or more halogen atoms, in particular $CF_3$, or an aryl group with 6 to 14 carbon atoms, if appropriate an alkyl group can bridge the carbon atoms in positions 3 and 4 of the phosphole ring carrying, respectively, the substituents R₃ and R₄, so as to form a ring with 3 to 8 carbon atoms;

R₅ represents a hydrogen atom, a heterocycle with five or six members having from 1 to 4 nitrogen or sulphur atoms, or a
linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms, optionally substituted by one or more groups, identical or different, chosen from a halogen atom, in particular F, Cl, Br or I, in particular F, an alkyl group with 1 to 6 carbon atoms, optionally substituted by one or more halogen atoms, in particular $CF_3$, or an aryl group with 6 to 14 carbon atoms;

in combination with a pharmaceutically acceptable vehicle.

According to a particular embodiment of the pharmaceutical composition comprising at least one compound of formula (VIII) as defined above:
R₁ represents a cycloalkyl group with 3 to 7 carbon atoms or an aryl group with 6 to 14 carbon atoms, and more particularly a cyclohexyl or phenyl group;
R₂ represents a nitrogen-containing heteroaryl group with six atoms having from 1 to 3 nitrogen atoms, and more particularly the 2-pyridyl group;
R₃ and R₄ represent independently of one another an alkyl group with 1 to 6 carbon atoms, and more particularly an alkyl group with 3 or 4 carbon atoms linking the atoms in positions 3 and 4 of the phosphole ring;
R₅ represents an aryl group with 6 to 14 carbon atoms, a thienyl group with 6 to 14 carbon atoms, or a pyridyl group with 6 to 14 carbon atoms, substituted or non-substituted, and more particularly a phenyl, 2-thienyl or 2-pyridyl group.

The invention relates more particularly to a pharmaceutical composition comprising a compound of formula (VIII) as defined above, characterized in that it comprises as active ingredient at least one compound of the following formula:

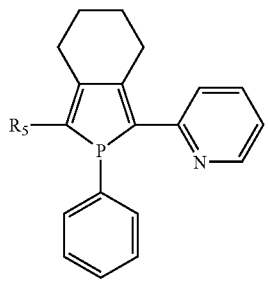

in which R₅ is as defined above.

According to another preferred embodiment of the composition comprising at least one compound of formula (VIII) as defined above, said composition comprises as active ingredient at least one compound of the following formula:

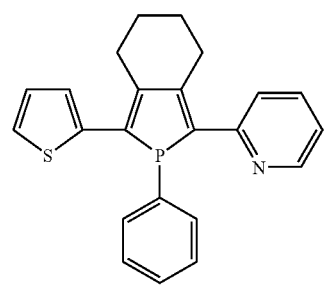

(5)

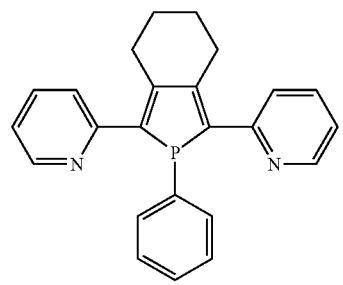

(6)

The invention also relates to any pharmaceutical composition as defined above, characterized in that it comprises as active ingredient at least one compound of general formula (A), and more particularly of formula (I) to (VIII), as defined above, in combination with at least one anticancer compound such as cisplatin, mitomycin C, doxorubicin, etoposide, carmustine.

A more particular subject of the invention is therefore products comprising:
at least one compound of general formula (A), and more particularly of formula (I) to (VIII), as defined above,
and at least one anticancer compound, as defined above,
as combination products for simultaneous or separate use, or use spread over time, in cancer therapy.

Advantageously, the abovementioned combination products contain a product of formula (A), in particular of formula (I), and an anticancer agent in a ratio of approximately 0.1/1 to approximately 2.5/1 and, if appropriate, one or more pharmaceutically acceptable vehicles.

Preferably, the pharmaceutical compositions, or above-mentioned combination products, are presented in a form which can be administered by intravenous route.

Also advantageously, the dosage of the compounds of formula (A), in particular of formula (I), contained in the pharmaceutical compositions or above-mentioned combination products, is approximately 5 to approximately 200 mg/m$^2$/day or per cure.

The invention also relates to the use of at least one compound of general formula (I), and more particularly of formula (II) to (VIII), as defined above, for the preparation of a medicament intended for the prevention or treatment of pathologies linked to excessive glutathione reductase and/or thioredoxin reductase activity.

Excessive glutathione reductase and/or thioredoxin reductase activity can be detected by the following methods. They are based on the assay, either of the protein concentration, or the enzymatic activity, or the catalyzed reaction product concentration (glutathione, thioredoxin), or the mRNA concentration.

The excess of protein is difficult to detect by Western-blot, because of the low content of these enzymes in the cell. Anti-glutathione reductase antibodies and anti-thioredoxin reductase antibodies exist.

The most reliable method involves taking a precise number of cells, preparing an extract and measuring the enzymatic activity by standard spectrophotometry, by measuring the oxidation of the NADPH during the reduction of the glutathione disulphide or the oxidized thioredoxin. Comparison of the activity obtained with that of the same number of healthy cells, as a control, makes it possible to evaluate the excess disulphide reductase activity.

Another method also involves measuring the redox potential in a single cell by electrochemical method. As the glutathione is the main thiol in the cell, measurement of the redox potential in the cytosol makes it possible to produce a very precise image of the GSH/GSSG ratio. In order to know the thioredoxin/reduced thioredoxin ratio, the same treatment must be carried out in the presence of diamide.

There are numerous methods for measuring the glutathione level. However, they have all the fault of producing a somewhat imprecise image of reality. When an extracted cell is prepared, numerous reactions (oxidation in air, cell lysis conditions etc.) modify the initial reduced glutathione/glutathione oxide ratio. The results in the literature are thus somewhat unreliable.

Generally it is more at the level of the mRNA that the excess can be detected by Northern-blot.

Among the pathologies linked to excessive glutathione reductase and/or thioredoxin reductase activity, capable of being treated within the framework of the present invention, there can in particular be mentioned:
cancers, namely all liquid or solid tumours, and more particularly cancers associated with infection by the Epstein-Barr virus,
rheumatoid arthritis,
psoriasis or psoriatic rheumatism,
Sjögren's syndrome,
infection with the HIV virus and associated diseases such as Kaposi's carcinoma.

The present invention also relates to the use of at least one compound of formula (VIII) as defined above, for the preparation of a medicament intended for the treatment of cancers.

A subject of the invention is also the use of at least one compound of general formula (A), and more particularly of formula (I) to (VIII), as defined above, for the preparation of a medicament intended for the prevention or treatment of phenomena of resistance to anticancer medicaments such as cisplatin, mitomycin C, doxorubicin, etoposide, carmustine, and, if appropriate, anti-infectious medicaments such as metronidazole, isoniazid.

The present invention also relates to the compounds of general formula (IX) below:

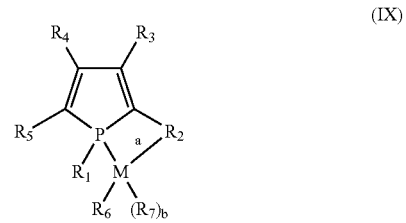

(IX)

in which:
a represents a single bond or no bond,
b represents 0 or 1,
$R_1$ represents a
linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, in particular F, Cl, Br, or I, in particular F, a linear or branched alkyl group with 1 to 6 carbon atoms, optionally substituted by one or more halogen atoms, in particular $CF_3$, or an aryl group with 6 to 14 carbon atoms;
$R_2$ represents a nitrogen-containing heteroaryl group or a nitrogen-containing heterocycle with 5 or 6 atoms having from 1 to 4 nitrogen atoms;
$R_3$ and $R_4$ represent, independently of one another, a hydrogen atom, or a
linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, in particular F, Cl, Br, or I, in particular F, a linear or branched alkyl group with 1 to 6 carbon atoms, optionally substituted by one or more halogen atoms, in particular $CF_3$, or an aryl group with 6 to 14 carbon atoms, if appropriate an alkyl group can bridge the carbon atoms in positions 3 and 4 of the phosphole ring carrying, respectively, the substituents $R_3$ and $R_4$, so as to form a ring with 3 to 8 carbon atoms;

$R_5$ represents a hydrogen atom, a heterocycle with five or six members having from 1 to 4 nitrogen or sulphur atoms, or a linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms, optionally substituted by one or more groups, identical or different, chosen from a halogen atom, in particular F, Cl, Br, or I, in particular F, a linear or branched alkyl group with 1 to 6 carbon atoms, optionally substituted by one or more halogen atoms, in particular $CF_3$, or an aryl group with 6 to 14 carbon atoms;

M represents a divalent, trivalent or tetravalent metal atom, providing that when M represents a divalent metal atom then a represents no bond and b is 0, when M represents a trivalent metal atom then a represents no bond and b is 1 and that when M represents a tetravalent metal atom then a represents a single bond and b is 1, $R_6$ represents a thio-osidic group with 3 to 60 carbon atoms, optionally substituted by one or more groups, identical or different, chosen from the protective groups of hydroxyl and amine groups, such as an alkanoyl group with 2 to 6 carbon atoms, or an arylcarbonyl group with 6 to 14 carbon atoms, $R_7$ represents
a halogen atom,
a thio-osidic group with 3 to 60 carbon atoms, optionally substituted by one or more groups, identical or different, chosen from the protective groups of hydroxyl and amine groups, such as an alkanoyl group with 2 to 6 carbon atoms, or an arylcarbonyl group with 6 to 14 carbon atoms,
a peptide group comprising from 1 to 5 amino acids, at least one of the amino acids comprising a thio group, such as S-cysteine or S-glutathione, or
a linear or branched thioalkyl group with 1 to 6 carbon atoms, a saturated or unsaturated thiocycloalkyl group with 3 to 7 carbon atoms or a thioaryl or thioheteroaryl group with 6 to 14 carbon atoms, such as a thiophenyl, 2-thiopyridyl or 4-thiopyridyl group, optionally substituted by one or more groups, identical or different, chosen from a halogen atom, in particular F, Cl, Br, or I, in particular F, an alkyl group with 1 to 6 carbon atoms, optionally substituted by one or more halogen atoms, in particular $CF_3$, or an aryl group with 6 to 14 carbon atoms.

In a particular embodiment, the present invention relates to a compound of general formula (IX) defined above, corresponding more particularly to the compound of general formula (X):

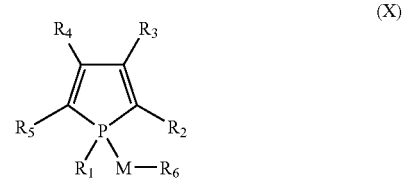

in which $R_1$, $R_2$, $R_3$, $R_4$, $R_5$ and $R_6$ are as defined above, and M represents a divalent metal atom, such as Au.

In another particular embodiment, the invention relates to a compound of general formula (IX) or (X) defined above, corresponding more particularly to the compound of general formula (XI):

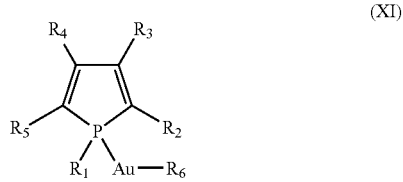

in which $R_2$, $R_3$, $R_4$, $R_5$ and $R_6$ are as defined above.

In another particular embodiment, the invention relates to a compound of formula (IX), (X), or (XI) in which:

$R_1$ represents a cycloalkyl group with 3 to 7 carbon atoms or an aryl group with 6 to 14 carbon atoms, and more particularly a cyclohexyl or phenyl group;

$R_2$ represents a nitrogen-containing heteroaryl group with six atoms having from 1 to 3 nitrogen atoms, and more particularly the 2-pyridyl group;

$R_3$ and $R_4$ represent independently of one another an alkyl group with 1 to 6 carbon atoms, and more particularly an alkyl group with 3 or 4 carbon atoms linking the atoms in positions 3 and 4 of the phosphole ring;

$R_5$ represents an aryl group with 6 to 14 carbon atoms, a thienyl group with 6 to 14 carbon atoms, or a pyridyl group with 6 to 14 carbon atoms, substituted or non-substituted, and more particularly a phenyl, 2-thienyl or 2-pyridyl group;

$R_6$ represents a thio-monosaccharide, in particular chosen from a thiopentose or a thiohexose, or a thiodioside, optionally substituted by one or more protective groups of the hydroxyl or amine groups, and more particularly thioglucose, thioglucose tetraacetate, thiomannose, thiomannose tetraacetate, thiogalactose, thiogalactose tetraacetate, thioribose, thioribose triacetate, thioxylose, thioxylose triacetate, thio-allose, thio-allose tetraacetate, thiotalose, thiotalose tetraacetate, thiofucose, thiofucose tetraacetate, thio-N-acetyl-glucosamine, thio-N-acetyl-glucosamine triacetate, thio-N-acetyl-galactosamine, thio-N-acetyl-galactosamine triacetate, thio-N-acetyl mannosamine, thio-N-acetyl mannosamine triacetate, thiolactose, thiolactose hepta-acetate;

if appropriate, $R_7$ represents a halogen, and more particularly a chlorine atom, a thio-monosaccharide, in particular chosen from a thiopentose or a thiohexose, or a thiodioside, optionally substituted by one or more protective groups of the hydroxyl or amine groups, and more particularly thioglucose, thioglucose tetraacetate, thiomannose, thiomannose tetraacetate, thiogalactose, thiogalactose tetraacetate, thioribose, thioribose triacetate, thioxylose, thioxylose triacetate, thio-allose, thio-allose tetraacetate, thiotalose, thiotalose tetraacetate, thiofucose, thiofucose tetraacetate, thio-N-acetyl-glucosamine, thio-N-acetyl-glucosamine triacetate, thio-N-acetyl-galactosamine, thio-N-acetyl-galactosamine triacetate, thio-N-acetyl mannosamine, thio-N-acetyl mannosamine triacetate, thiolactose, thiolactose heptaacetate.

The invention relates more particularly to a compound of formula (IX), (X) or (XI) as defined above, of formula (XII) below:

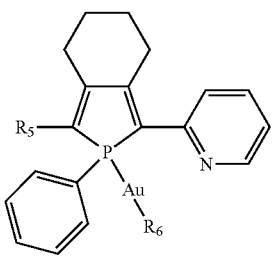

(XIII)

in which $R_5$ and $R_6$ are as defined above.

In a preferred embodiment, the invention relates to a compound of formula (IX), (X), (XI) or (XII) corresponding more particularly to the compound of formula (8) below:

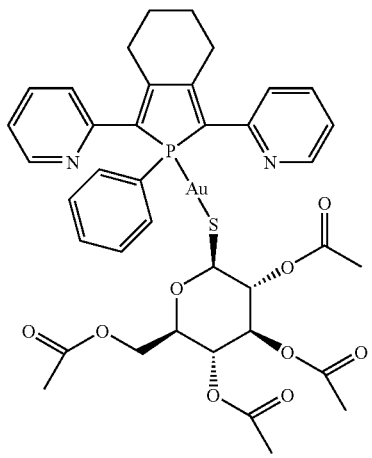

(8)

Advantageously the compounds of formula (IX), (X), (XI), (XII), or (8) are soluble in aqueous solvents and stable over time. The sugar (osidic) part protected at the level of the hydroxyl groups, for example by alkanoyl groups, such as acetates, confers an oral permeability whereas a non-protected sugar part (free hydroxyl functions) confers a similar activity on the protected complex but with administration by injectable route.

The invention is further illustrated using the following detailed description of the synthesis of phosphole derivatives used within the framework of the present invention, and of the demonstration of their properties in the inhibition of human GR and TrxR.

The 2-pyridylphospholes are accessible by various methods known to a person skilled in the art. The following references can be mentioned: (a) C. Hay, D. Le Vilain, V. Deborde, L. Toupet, R. Réau Chem. Commun., 1999, 345-346 (b) Holand, S.; Jeanjean, M.; Mathey, F. Angew. Chem., Int. Ed. 1997, 36, 98. (c) M. Sauthier, F. Leca, L. Toupet, R. Réau Organometallics, 2002, 3 21, 1591.

More particularly, the following 2-pyridylphospholes (5) and (6) are described in publications (a) and (c), respectively.

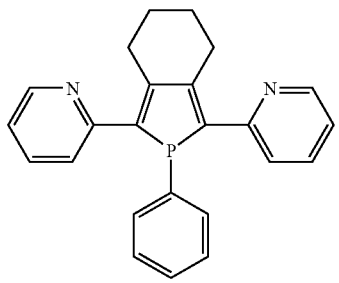

(5)

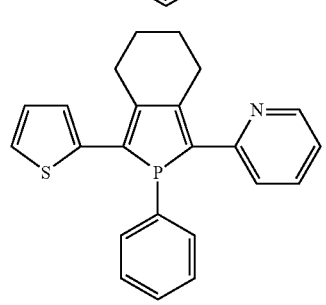

(6)

The reaction of a compound (5) or (6) with a complex of formula LAuX or $HAuCl_4, 3H_2O$ in order to obtain the above-mentioned corresponding complex of formula (1) or (2) can be carried out under an inert atmosphere (argon, nitrogen) in a usual organic solvent at a temperature comprised between −90° C. and +80° C.

The compounds (1) and (2) are purified by standard purification methods (washing and cold crystallization). These compounds are described in the report for the Diploma of Advanced Studies in Molecular Chemistry by N. Lessen, University of Rennes 1, June 2002.

The reaction of a compound (5) or (6) with a complex of formula $L_2PtX_2$ in order to obtain the corresponding complex (3) or (4) can be carried out under an inert atmosphere (argon, nitrogen) in a usual organic solvent at a temperature comprised between −90° C. and +80° C. The compounds (3) and (4) are purified by standard purification methods (washing and cold crystallization).

These compounds are described in the Doctoral thesis of the University of Rennes 1 by C. Fave, October 2003.

In the abovementioned precursors LAuX and $L_2PtX_2$, L can be a Lewis base-type ligand, and more particularly a sulphur-containing ligand such as dimethylsulphide or tetrahydrothiophene, or a nitrogen-containing ligand such as acetonitrile or benzonitrile. X is a halogen atom, as defined previously. These complexes are commercially available or accessible by the methods known to a person skilled in the art.

Compound (8) is obtained by deprotonating the thiol function of 1-thio-β-D-glucose-tetraacetate in an organic solvent then reacting it with compound (1).

As usual organic solvent, it is possible to use aromatic hydrocarbons (benzene, toluene etc.), ethers (diethylether, tetrahydrofuran etc.), halogenoalkanes (dichloromethane, chloroform etc.) as well as aliphatic alcohols (methanol, ethanol etc.).

DESCRIPTION OF FIG. 1

FIG. 1 represents the increase in the volume of tumours (y-axis, in percentages) implanted in the brains of 4 control rats (histogram on the left) and of 4 rats treated with the complex (1) (histogram on the right) at a dose of 25 mg/kg administered by intravenous route three times consecutively during the development of the tumour.

EXAMPLES

Examples 1 to 5 below are presented in order to illustrate the synthesis procedures and should in no event be considered as limiting the scope of the invention.

Example 1

Synthesis of Complex (1)

AuCl (tetrahydrothiophene) (0.026 g, 0.081 mmol) in the form of powder is added at ambient temperature to a $CH_2Cl_2$ solution (10 mL) of 1-phenyl-2,5-di(2-pyridyl)phosphole (5) (0.030 g, 0.081 mmol). The mixture is left for three hours under stirring at ambient temperature, then the volatile products are evaporated off under vacuum. The solid is washed with pentane (4×10 mL) and complex (1) is obtained in the form of a solid which is stable in air (0.034 g, 70% yield).

$^1$H NMR (300 MHz, CDCl$_3$): δ 1.85 (m, 4H), 3.06 (m, 2H), 3.24 (m, 2H), 7.09 (dd, J (H, H)=7.2 Hz, J (H, H)=4.7 Hz, 2H), 7.30 (m, 3H), 7.68 (m, 6H), 8.51 (d, 2H, J (H, H)=4.7 Hz), $^{13}$C-{$^1$H} NMR (CDCl$_3$; 75.46 MHz): δ 22.7 (s), 30.0 (s), 30.2 (s), 122.8 (s), 124.5 (d, J (P, C)=5.5 Hz), 129.3 (d, J (P, C)=12.4 Hz), 132.2 (s), 134.5 (d, J (P, C)=14.0 Hz) 137.2 (s), 149.4 (s), 152.2 (d, J (P, C)=13.9 Hz), 153.6 (m); certain quaternary carbon atoms are not observed, $^{31}$P-{$^1$H} NMR (CDCl$_3$, 121.5 MHz): δ+39.9 (s), High-resolution mass spectrometry (mNBA, FAB): (m/z) 601.0859 [M+H]$^+$, UV-Vis, (CH$_2$Cl$_2$) λmax (nm), ε (M$^{-1}$ cm$^{-1}$): 271 (7850), 383 (8300), Emission (CH$_2$Cl$_2$) λ em (nm): 495.

Example 2

Synthesis of Complex (2)

AuCl (tetrahydrothiophene) (0.079 g, 0.25 mmol) in the form of powder is added at ambient temperature to a $CH_2Cl_2$ solution (10 mL) of 1-phenyl-2-(2-pyridyl)-5-(2-thienyl)phosphole (6) (0.092 g, 0.25 mmol). The mixture is left for three hours under stirring at ambient temperature, then the volatile products are evaporated off under vacuum, The solid is washed with pentane (4×10 mL) and complex (2) is obtained in the form of a solid which is stable in air (0.105 g, 70% yield), $^1$H NMR (300 MHz, CDCl$_3$): δ 1.85-2.10 (m, 4H), 2.95-3.35 (m, 4H), 6.99 (dd, J (H, H)=4.5 Hz, 3 J (H, H)=4.0 Hz, 1H), 7.11 (ddd, J (H, H)=2.3 Hz, J (H, H)=4.6 Hz, J (H, H)=6.8 Hz, 1H), 7.44-7.52 (m, 2H), 7.65-7.59 (m, 2H), 7.77 (ddd, J (H, H)=1.3 Hz, J (H, H)=7.4 Hz, J (H, H)=8.0 Hz, 1H), 8.52 (dd, 2H, J (H, H)=4.6 Hz, J (H, H)=1.6 Hz), $^{13}$C-{$^1$H} NMR (CDCl$_3$; 75.46 MHz): δ 22.7 (s), 22.8 (s), 29.7 (d, J (P, C)=10.2 Hz), 30.5 (d, J (P, C)=9.9 Hz), 122.4 (s), 123.5 (d, J (P, C)=7.1 Hz), 127.8 (s), 128.1 (s), 128.8 (d, J (P, C)=7.8 Hz), 129.6 (d, J (P, C)=12.5 Hz), 132.5 (d, J (P, C)=3.1 Hz), 134.4 (d, J (P, C)=14.0 Hz) 136.7 (s), 149.7 (s); certain quaternary carbon atoms are not observed, $^{31}$P-{$^1$H} NMR (CDCl$_3$, 121.5 MHz): δ+40.2 (s), High-resolution mass spectrometry (mNBA, FAB): (m/z) 606.0 [M+H]$^+$.

Example 3

Synthesis of Complex (4)

(PhCN)$_2$PtCl$_2$ (0.128 g, 0.27 mmol) in the form of powder is added at ambient temperature to a $CH_2Cl_2$ solution (10 mL) of 1-phenyl-2,5-di(2-pyridyl)phosphole (5) (0.10 g, 0.27 mmol). The mixture is left for one hour under stirring at ambient temperature, then the volatile products are evaporated off under vacuum. The solid is washed with diethyl ether (3×10 mL) and complex (3) is obtained in the form of a solid which is stable in air (86% yield), $^1$H NMR (300 MHz, CDCl$_3$): δ 1.70-2.00 (m, 4H), 2.50-2.75 (m, 1H), 2.85-3.22 (m, 3H), 7.08 (dd, J (H, H)=7.3 Hz, 3 J (H, H)=4.9 Hz, 1H), 7.72-8.00 (m, 9H), 8.55 (d, J (H, H)=8.0 Hz, 1H), 8.65 (d, J (H, H)=4.1 Hz, 1H), 9.94 (d, J (H, H)=6.1 Hz, 1H), $^{13}$C-{$^1$H} NMR (CDCl$_3$; 75.46 MHz): δ 21.2 (s), 22.8 (s), 28.1 (d, J (P, C)=9.4 Hz), 30.6 (d, J (P, C)=10.1 Hz), 123.0 (s), 124.2 (s), 127.9 (s), 129.4 (d, J (P, C)=12.2 Hz), 129.5 (s), 132.9 (d, J (P, C)=2.8 Hz), 134.2 (d, J (P, C)=12.7 Hz), 139.2 (s), 149.8 d, J (P, C)=13.6 Hz), 149.5 (s), 149.8 (d, J (P, C)=12.1 Hz), 152.1 (d, J (P, C)=18.4 Hz), 152.8 (d, J (P, C)=14.0 Hz), 153.1 (s).

$^{31}$P-{$^1$H} NMR (CDCl$_3$, 121.5 MHz): δ+35.7 (s, J (P, Pt)=3712 Hz),

High-resolution mass spectrometry (oNPOE, FAB): (m/z) 635.0568 [M+H]$^+$.

Example 4

Synthesis of Complex (4)

(PhCN)$_2$PtCl$_2$ (0.09 g, 0.20 mmol) in the form of powder is added at ambient temperature to a $CH_2Cl_2$ solution (10 mL) of 1-phenyl-2-(2-pyridyl)-5-(2-thienyl)phosphole (6) (0.07 g, 0.20 mmol). The mixture is left for one hour under stirring at ambient temperature, then the volatile products are evaporated off under vacuum. The solid is washed with diethyl ether (3×10 mL) and complex (4) is obtained in the form of a solid which is stable in air (0.11 g, 86% yield), $^1$H NMR (300 MHz, CDCl$_3$): δ 1.62-2.00 (m, 4H), 2.60-2.73 (m, 2H), 3.07-2.86 (m, 2H), 7.65-7.59 (m, 2H), 6.26 (d, J (H, H)=4.3 Hz, 1H), 7.10-7.90 (m, 9H), 9.88 (d, 2H, J (H, H)=5.8 Hz), $^{13}$C-{$^1$H} NMR (CDCl$_3$; 75.46 MHz): δ 21.5 (s), 22.4 (s), 27.9 (d, J (P, C)=9.3 Hz), 29.5 (d, J (P, C)=10.6 Hz), 122.4 (s), 123.4 (d, J (P, C)=9.7 Hz), 123.5 (s), 124.3 (d, J (P, C)=57.3 Hz), 127.7 (s), 128.8 (d, J (P, C)=12.4 Hz), 129.1 (s), 130.5 (d, J (P, C)=60.6 Hz), 132.6 (d, J (P, C)=2.9 Hz), 133.5 (d, J (P, C)=12.9 Hz), 133.9 (d, J (P, C)=4.1 Hz), 135.3 (d, J (P, C)=19.4 Hz), 135.8 (d, J (P, C)=57.5 Hz), 138.9 (s), 148.3 (d, J (P, C)=15.8 Hz), 150.8 (d, J (P, C)=12.0 Hz), 152.1 (s), $^{31}$P-{$^1$H} NMR (CDCl$_3$, 121.5 MHz): δ+37.3 (s, J (P, Pt)=3704 Hz).

High-resolution mass spectrometry (mNBA, FAB): (m/z) 602.0375 [M-Cl]$^+$.

Example 5

Synthesis of complex (8)

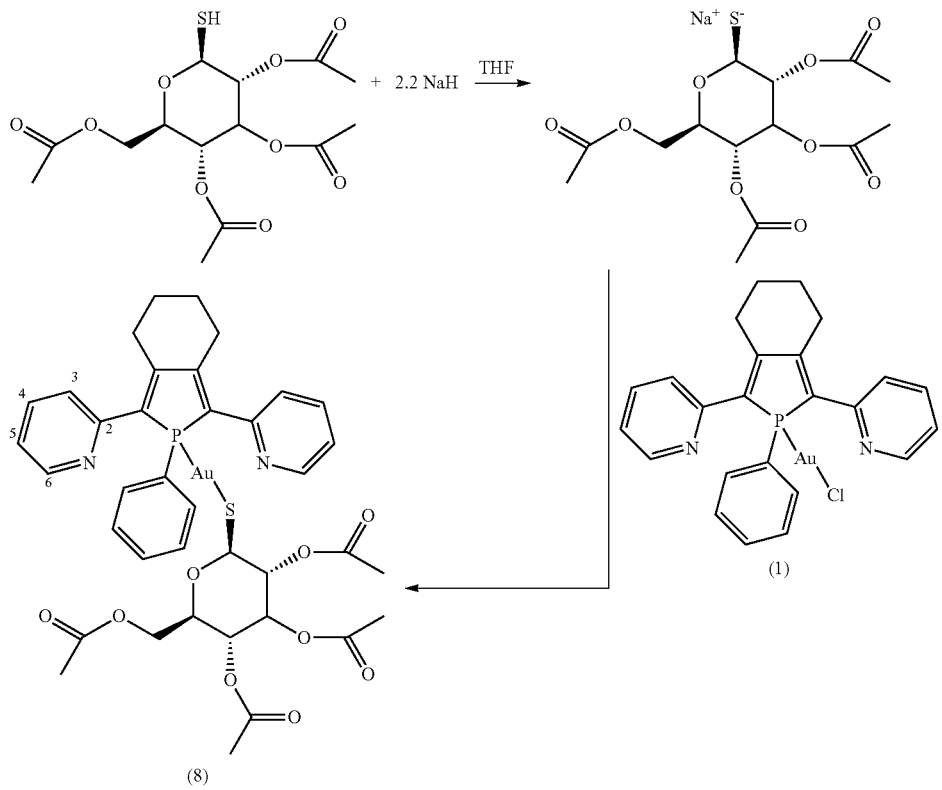

2.2 equivalents of NaH (0.014 g; 0.61 mmol) are added to a solution of 1-thio-β-D-glucose-tetraacetate (0.100 g; 0.28 mmol) in THF (10 mL). The solution is left under stirring for 90 minutes, then one equivalent of complex (1) (0.165 g; 0.028 mmol) is added. The resulting mixture is left under stirring for 90 minutes. The solution is concentrated to one quarter under vacuum, then ether (20 mL) is added. Stirring is continued for 10 minutes. The supernatant is collected and the solid residue is extracted once more with ether (20 mL). The liquid phases are combined and the solvents are eliminated under vacuum. The complex (8) is then purified by chromatography on a silica gel column with an ether/ethyl acetate mixture (65/35) as eluent. Complex (8) is obtained in the form of a yellow powder with a yield of 62%.

$^1$H NMR (CDCl$_3$, 200 MHz): δ=1.77 (s, 3H, CH$_3$ sugar), 1.73-1.88 (m, 4H, =CCH$_2$CH$_2$), 1.99 (s, 3H, CH$_3$ sugar), 2.00 (s, 3H, CH$_3$ sugar), 2.02 (s, 2H, CH$_2$ sugar), 2.07 (s, 3H, CH$_3$ sugar), 2.91-3.10 (m, 2H, =CCH$_2$), 3.22-3.42 (m, 2H, =CCH$_2$), 3.64-3.74 (m, 1H, CH sugar), 3.95-4.16 (m, 2H, CH sugar), 4.88-5.2 (m, 2H, CH sugar), 7.03-7.15 (m, 2H, H$^5$ Py), 7.23-7.31 (m, 3H, H$_{meta}$ Ph, H$_{para}$ Ph), 7.58-7.81 (m, 6H, H$^4$ Py, H$^3$ Py, H$_{ortho}$ Ph), 8.53 (broad d, J$_{HH}$=4.7 Hz, 1H, H$^6$ Py), 8.60 (dl, J$_{HH}$=4.7 Hz, 1H, H$^6$ Py).

$^{13}$C{$^1$H}NMR (CD$_2$Cl$_2$, 75.469 MHz): δ=20.4 (s, CH$_3$ sugar), 22.3 (s, =CCH$_2$CH$_2$), 29.7 (s, =CCH$_2$), 29.8 (s, =CCH$_2$), 29.9 (bs, =CCH$_2$), 62.7 (s, C sugar), 68.8 (s, C sugar), 74.1 (s, C sugar), 75.7 (s, C sugar), 77.6 (s, C sugar), 83.0 (s, C sugar), 122.2 (s, C$^5$ Py), 122.3 (s, C$^5$ Py), 123.7 (d, J$_{PC}$=6.4 Hz, C$^3$ Py), 123.9 (d, J$_{PC}$=6.3 Hz, C$^3$ Py), 128.7 (s, m-Ph), 128.9 (s, m-Ph), 131.3 (s, p-Ph), 131.4 (s, p-Ph), 133.9 (s, o-Ph), 134.1 (s, o-Ph), 136.5 (bs, C$^4$ Py), 149.2 (s, C$^6$ Py), 149.3 (s, C$^6$ Py), 152.1 (s, C$^2$ Py), 152.3 (s, C$^2$ Py), 153.01 (d, J$_{PC}$=6.3 Hz, P—C=C), 153.46 (d, J$_{PC}$=6.1 Hz, P—C=C), 169.3 (s, C=O sugar), 169.4 (s, C=O sugar), 169.9 (s, C=O sugar), 170.4 (s, C=O sugar).

$^{31}$P{$^1$H} NMR (CDCl$_3$, 81.0 MHz) δ=+47.3 ppm (broad s);

HR-MS (ESI, CH$_2$Cl$_2$): m/z 951.1768 (M$^+$+Na$^+$: calculated 951.1755)

Example 6

Study of the Human GR and TrxR Inhibition Properties of the Compounds (1) to (4)

The phosphole derivatives containing gold and platinum have been identified as powerful inhibitors of human GR and TrxR (see Table 1). With either the substrate TrxC72S, or DTNB, very low IC50 values at nanomolar level—quasi-stoichiometric reaction—were obtained with wild-type human TrxR. By contrast, the IC50 values with the Sec→Cys mutant were at least 1000 times higher, proving that the selenocysteine residue is the inhibition target of human TrxR. Human GR was very effectively inhibited by the gold complexes and less effectively by those of platinum (see Table 1). A reduction of these enzymes is necessary to complete the inhibition, which proves that the active site comprising the Cys/Cys residues in the GR or Cys/Sec in the TrxR is the inactivation site. The pre-reduction of these enzymes accelerates the inhibition. The reaction between the inhibitor and these enzymes is very rapid and not precisely measurable with standard enzymology techniques. The inhibitors exhibit very weak competition with GSSG and Trx with Ki values on the low μM scale. This competition would probably not contribute to the irreversible enzymatic inactivation.

The stoichiometry of binding of (1) to human GR was determined by titration. Based on these experiments, (1) binds very tightly to the binding site of the GSSG of each human GR sub-unit. The value of the disassociation constant Kd=Ki=[human GR][(1)]/[human GR*(1)], determined from the kinetics measured at initial speed with 0.5-2.0 μM GSSG, was 0.46 μM. The differences in the extinction coefficient at selected wavelengths have revealed a stoichiometry of 1.25 equivalents of (1) per FAD or per sub-unit of human GR. Although numerous hydrophobic inhibitors of the human GR and of the GR of *Plasmodium falciparum* are bound in the cavity between the two sub-units of the dimer with a stoichiometry of 0.5 per sub-unit, this is not the case for the inhibitor (1). The stoichiometry of 1.25 equivalents of (1) per FAD or per sub-unit of human GR can be explained by the presence of a second molecule of (1) bound less tightly to another position in the human GR, confirming the 3D structure of the complex GR-(1). The three-dimensional structure of alkylated human GR in fact shows two binding sites for the metallo-phosphole (1):

the gold (Au) atom is covalently bound between the Cys58 and the Cys63 which form the redox centre of the active site. The inactivation mechanism of human GR therefore involves an S—Au(I)—S coordination and the loss of the phosphole ligand;

the second site for the metallo-phosphole (1) is the Cys284 exposed to the solvent, at 23 Å of the active site and located in a hydrophobic cavity. In this case, the sulphur atom of the Cys284 remains bound to the Au-phosphole entity.

Based on kinetic studies as well as on the preliminary radiocrystallography data, (1) reacts with the Cys58 and/or the Cys63 of the human GR according to the sequential order of the addition of the reagents in the pre-incubation medium, i.e. pre-reduction of the enzyme by the reducing agent then reaction with the inhibitor, or pre-reaction of the enzyme with the inhibitor then reduction by the reducing agent. Whatever the sequential order chosen, the human GR molecules modified by (1) no longer have a catalytic activity. In conclusion, (1) binds tightly to the GSSG binding site of each sub-unit of human GR (Eox) with a Kd on a submicromolar scale. Moreover, the inhibitor forms a covalent bond with the Cys58 and/or the Cys63 of the reduced enzyme, which leads to complete inactivation of the human GR.

On the basis of the essential functions of human TrxR and GR in the cell redox equilibrium, promotion of cell growth, DNA synthesis, redox-dependent regulation processes as well as resistance to medicaments, these proteins serve as promising targets for the development of chemotherapy agents against tumours, parasites, insects, and other diseases characterized by inflammation and/or intense cell proliferation (such as rheumatoid arthritis, Sjögren's syndrome, psoriasis). The phospholes (1) to (4) as well as their derivatives are highly effective as inhibitors of human TrxR and GR and can therefore serve as potential medicaments for the chemotherapy of the diseases mentioned above as well as for studying the cell redox metabolism.

In the preliminary experiments, the inhibitors are active against the human cells of glioblastomas on a micromolar scale.

Example 7

Tests of in Vitro Proliferation of the Complex (1) and Analogues (2)-(6) and (8)

The BrdU Labelling and Detection Kit III (Roche Diagnostics, Mannheim, Germany) was used in order to determine the DNA synthesis of different cell lines of human glioblastomas (NCH37, NCH82 and NCH 89) in the presence of the different compounds (1-8).

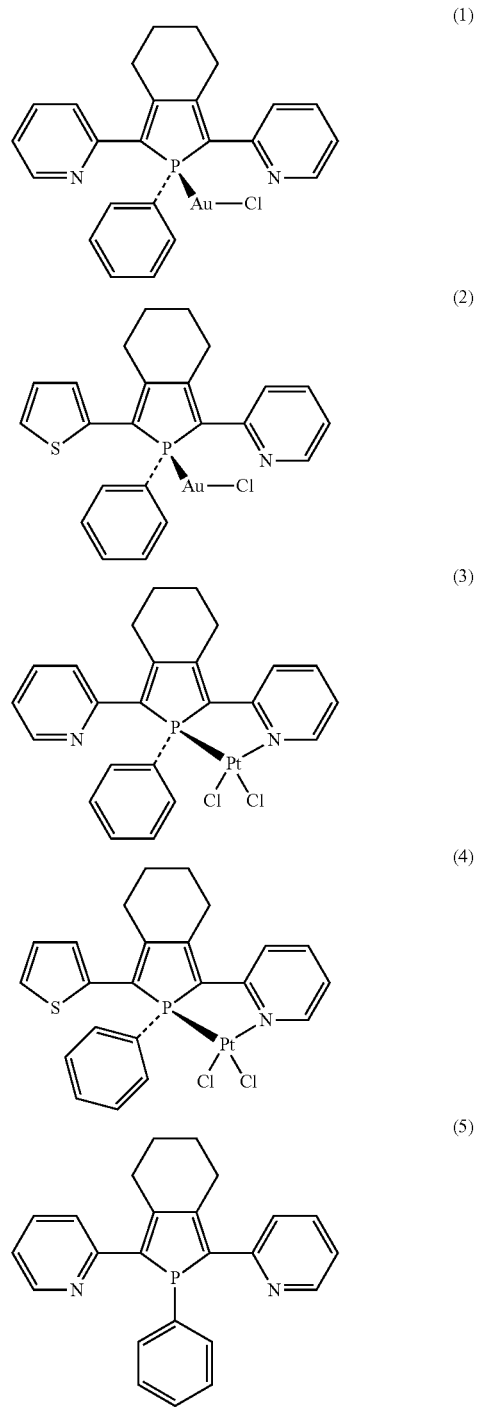

(6)

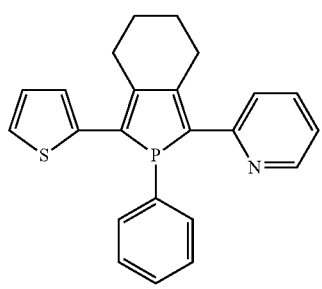

(7)

(8)

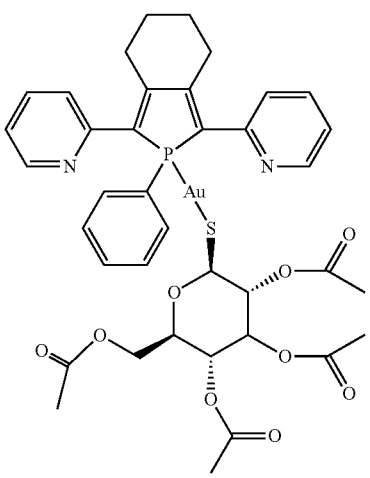

Briefly, the tumour cells are cultured and duplicated in 96-well plates in RPMI 1640 medium containing 10% foetal calf serum and antibiotics (cell density: $7 \times 10^3$ cells). After 24 hours the compounds (1)-(8) were added at different concentrations. After 48 hours, the reagent 5-bromo-2'-deoxyuridine (BrdU) was added at the final concentration of 10 μM for an incubation period of 19 hours. The mean absorbency value of the control samples containing no compounds (1)-(8) is defined at 100% as the maximum proliferation value. Compound (7) (Au-triphenylphosphine chloride complex, (PPh$_3$)AuCl) and nitrosourea 1,3-bis(2-chloroethyl)-1-nitrosourea (BCNU, carmustine) are positive controls already reported in the literature. The different glioblastoma cell lines tested are resistant to carmustine, which is a medicament commonly used in anticancer therapy, as a cytostatic agent against brain tumours.

Under these conditions, the most powerful anti-proliferative effects amongst the derivatives (1)-(8) are observed (Table 2), after treatment, for the complex (8), followed by the compound (1), the compound (2), and the compound (7) ((PPh$_3$)AuCl) with IC$_{50}$ values on a micromolar scale. The compounds (5) and (6) also have an anti-proliferative effect greater than that of compound (7) on the cell line NCH89. By comparison, carmustine displayed 50% inhibition of the growth of the glioblastoma cell lines NCH37, NCH82, and NCH89 at 300±12, 385±25, and 615±38 μM, respectively.

Example 8

Antineoplastic Activity of the Complex (1) In Vivo in Rats

The antineoplastic activity of the complex was tested in rats. The model for orthopic inoculation of C6 rat glioma cells is an in vivo model well known for analyzing and evaluating the therapeutic effects of molecules against malignant gliomas.

The C6 rat glioma cells were implanted in the brain of male Wistar rats aged from 6 to 8 weeks. The rats' heads were fixed in a frame with stereotactic orientation, and $5 \times 10^5$ tumour cells were inoculated (laterally 4 mm from the bregma and at a depth of 5-6 mm under the dura mater). The sizes of the tumours in the rats' brains were determined by conventional magnetic resonance imaging (MRI). This was carried out on days 9 and 15 with a 2.35 Tesla Small-Bore MRI unit. Before imaging, a paramagnetic contrast agent was injected by intravenous route at a dose of 0.1 mL per 100 g of body weight. On the basis of the conventional MRI images, all the tumours could be well delimited from the brain tissue surrounding the tumour.

After confirmation of the tumour growth by MRI on day 9, the rats carrying tumours were treated by intravenous injection with the compound (1) at a concentration of 25 mg/kg (n=4). The tumour growth was compared to that of the non-treated control animals (n=4). The treatment commenced on day 9 and continued on days 11 and 13. On day 15 after the implantation of the tumour cells, all the rats were sacrificed by decapitation. Under these conditions, a 44% reduction of the tumour growth was observed between days 9 and 15 at a dose of compound (1) of 25 mg/kg of body weight compared with that of the control group (FIG. 1).

The total body weight of the C6 rats carrying gliomas showed no significant difference between the two groups of treated or control animals. Similarly, no animal died from treatment with the compound (1) indicating that the therapy was well tolerated at 25 mg/kg.

Example 9

Binding of Complex 1 to DNA

In addition to its major activity on human disulphide reductases, glutathione reductase and thioredoxin reductase, the binding of complex (1) to DNA was measured in thermal DNA denaturation tests. Complex 1 proved to be active from 1 μM in the tests carried out at a concentration comprised between 0 and 20 μM of complex (1).

TABLE 1

Inhibition of human TrxR and GR by the phospholes P9-P12.
Conditions: 10 minutes of pre-incubation with 200 μM NADPH
(in the test for reduction of DTNB by TrxR) or with 100 μM NADPH
(in the test for reduction of Trx by TrxR, and the test for reduction of
GSSG by GR). Enzyme concentrations: with the mutant hTrxR-Mut,
DTNB test: 90.6 nM; Trx test: 1.8 μM; with the wild type hTrxR-Wt,
DTNB test: 4.8 nM, Trx test: 24 nM. The TrxR tests were carried out
either in the presence of 3 mM DTNB or 20 μM hTrxC72S; the
GR tests were carried out in the presence of 100 μM GSSG.

| Inhibitor | $IC_{50}$ WT hTrxR 3 mM DTNB/ 20 μM hTrxC72S | $IC_{50}$ hTrxRSec→Cys 3 mM DTNB/ 20 μM hTrxC72S | $IC_{50}$ human GR |
|---|---|---|---|
| (1) | 0.8 nM/7 nM | 2500 nM/800 nM | 1 nM |
| (2) | 1 nM/7 nM | 2500 nM/1400 nM | 2 nM |
| (3) | 1 nM/7 nM | 30000 nM/1400 nM | 1000 nM |
| (4) | 1 nM/8 nM | 24000 nM/2300 nM | 400 nM |

TABLE 2

Cytotoxic effects of compounds 1-8 on the in vitro proliferation of glioblastoma cell lines.

| Lines | $IC_{50}$ (μM) of the compounds | | | | | | | |
|---|---|---|---|---|---|---|---|---|
| | 1 | 2 | 3 | 4 | 5 | 6 | 7 | 8 |
| NCH37 | 5.4 ± 0.7 | 5.7 ± 0.2 | 33 ± 3.2 | 28.1 ± 0.8 | nd | nd | 6.1 ± 0.2 | nd |
| NCH82 | 12.5 ± 0.8 | 7.5 ± 0.04 | 65 ± 6.3 | 81.8 ± 4.1 | nd | nd | 7.2 ± 0.2 | 0.93 ± 0.06 |
| NCH89 | 10.8 ± 0.8 | 15.2 ± 0.4 | 43 ± 3.7 | 78.4 ± 3.1 | 6.7 ± 0.3 | 8.5 ± 0.5 | 20.3 ± 0.7 | 2.54 ± 0.45 | nd, not determined

REFERENCES

Arnér E S, Holmgren A. Physiological functions of thioredoxin and thioredoxin reductase. Eur J Biochem 2000; 267:6102-09.

Arnér E S, Nakamura H, Sasada T, Yodoi J, Holmgren A, Spyrou G. Analysis of the inhibition of mammalian thioredoxin, thioredoxin reductase and glutaredoxin by cis-diamminedichlorplatinum (II) and its major metabolite, glutathione-platinum complex. Free Rad Biol Med 2001; 31:1170-78.

Arscott L D, Gromer S, Schirmer R H, Becker K, Williams C H, Jr. The mechanism of thioredoxin reductase from human placenta is similar to the mechanisms of lipoamide dehydrogenase and glutathione reductase and is distinct from the mechanism of thioredoxin reductase from Escherichia coli. Proc Natl Acad Sci USA 1997; 94:3621-26.

Becker K, Gromer S, Schirmer R H, Muller S. Thioredoxin reductase as a pathophysiological factor and drug target. Eur J Biochem 2000; 267:6118-25.

Becker K, Herold-Mende C, Park J J, Lowe G, Schirmer R H. Human thioredoxin reductase is efficiently inhibited by (2,2':6',2"-terpyridine)platinum(II) complexes. Possible implications for a novel antitumor strategy. J Med Chem 2001; 44: 2784-92.

Becker K, Savvides S, Keese M, Schirmer R H & Karplus P A. Enzyme inactivation through sulfhydryl oxidation by physiologic NO-carriers. Nature Struct Biol 1998; 5: 267-271.

Davioud-Charvet E, Delarue S, Biot Ch, Schwöbel B, Boehme C C, Müssigbrodt A, Maes L, Sergheraert Ch, Grellier P, Schirmer R H, Becker K. A prodrug form of a Plasmodium falciparum glutathione reductase inhibitor conjugated with a 4-anilinoquinoline. J Med Chem 2001; 44: 4268-4276.

Davioud-Charvet E, McLeish M J, Veine D M, Giegel D, Arscott L D, Andricopulo A D, Becker K, Müller S, Schirmer R H, Williams Jr C H, Kenyon G L. Mechanism-based inactivation of thioredoxin reductase by Mannich bases. Implication for cytotoxicity. Biochemistry 2003; 42, 13319-13330.

Dimmock J R, Vashishtha S C, Quail J W, Pugazhenthi U, Zimpel Z, Sudom A M, Allen T M, Kao G Y, Balzarini J, De Clercq E. 4-(beta-Arylvinyl)-3-(beta-arylvinylketo)-1-ethyl-4-piperidinols and related compounds: a novel class of cytotoxic and anticancer agents. J. Med. Chem. 1998, 41, 4012-4020.

Engman L, Al-Maharik N, McNaughton M, Birmingham A, Powis G. Thioredoxin reductase and cancer cell growth inhibition by organotellurium antioxidants. Anticancer Drugs 2003; 14:153-61.

Fave, C. Doctoral thesis of the University of Rennes 1, No. 2900, October 2003.

Gladyshev V N, Jeang K T, Stadtman T C. Selenocysteine, identified as the penultimate C-terminal residue in human T-cell thioredoxin reductase, corresponds to TGA in the human placental gene. Proc Natl Acad Sci USA 1996; 93:6146-51.

Gromer S, Arscott L D, Williams C H, Jr., Schirmer R H, Becker K. Human placenta thioredoxin reductase. Isolation of the selenoenzyme, steady state kinetics, and inhibition by therapeutic gold compounds. J Biol Chem 1998; 273:20096-101.

Gromer S, Gross J H. Methylseleninate is a substrate rather than an inhibitor of mammalian thioredoxin reductase. Implications of the antitumor effects of selenium. J Biol Chem 2002; 277:9701-06.

Gromer S, Schirmer R H, Becker K. The 58 kDa mouse selenoprotein is a BCNU-sensitive thioredoxin reductase. FEBS Lett 1997; 412:318-20.

Gromer S, Wissing J, Behne D, et al. A hypothesis on the catalytic mechanism of the selenoenzyme thioredoxin reductase. Biochem J 1998; 332:591-92.

Hay, C., Hissler, M., Fischmeister, C., Rault-Berthelot, J., Toupet, L., Nyulaszi, L., Réau, R. Phosphole-containing p-conjugated systems: from model molecules to polymer films on electrodes. Chem. Eur. J., 2001, 7, 4222-4236.

Holmgren A. Antioxidant function of thioredoxin and glutaredoxin systems. Antioxid Redox Signal 2000; 2:811-20.

Husbeck B, Powis G. The redox protein thioredoxin-1 regulates the constitutive and inducible expression of the estrogen metabolizing cytochromes P450 1B1 and 1A1 in MCF-7 human breast cancer cells. Carcinogenesis 2002; 23:1625-30.

Irmler, A., Bechthold, A., Davioud-Charvet, E., Hofmann, V., Réau, R., Gromer, S., Schirmer, R. H., and Becker, K. (2002) Disulfide reductases—Current developments, pp 803-815. In *Flavins and Flavoproteins* 2002. Chapman, S. K., Perham, R. N., Scrutton N. S., Eds. Agency for Scientific Publications, Berlin, 2002.

Kahlos K, Soini Y, Saily M, Koistinen P, Kakko S, Paakko, P, Holmgren A, Kinnula V L. Up-regulation of thioredoxin and thioredoxin reductase in human malignant pleural mesothelioma. Int J Cancer 2001; 95:198-204.

Kim M R, Chang H S, Kim B H, Bask S H, Lee S R, Kim J R. Involvements of mitochondrial thioredoxin reductase (TrxR2) in cell proliferation. Biochem Biophys Res Comm 2003; 304:119-24.

Lin, S, Del Razo L M, Styblo M, Wang C, Cullen W R, Thomas D J. Arsenicals inhibit thioredoxin reductase in cultured rat hepatocytes. Chem Res Toxicol 2001; 14:305-11.

Lincoln D T, Ali Emadi E M, Tonissen K F, Clarke F M. The thioredoxin-thioredoxin reductase system: over-expression in human cancer. Anticancer Res 2003; 23:2425-33.

May J M, Morrow J D, Burk R F. Thioredoxin reductase reduces lipid hydroperoxides and spares alpha-tocopherol. Biochem Biophys Res Commun 2002; 292:45-49.

Nelsen, L. Rapport de DEA Chimie moléculaire [Report for the Diploma of Advanced Studies in Molecular Chemistry], University of Rennes 1, June 2002.

Powis G, Kirkpatrick D L, Angulo M, Baker A. Thioredoxin redox control of cell growth and death and the effects of inhibitors. Chem Biol Interact 1998; 111-112:23-34.

Ross S A, Carr C A, Briet J W, Lowe G. Transfer of 4'-chloro-2,2':6',2"-terpyridine platinum(II) between human serum albumin, glutathione and other thiolate ligands. A possible selective natural transport mechanism for the delivery of platinum (II) drugs to tumour cells. Anticancer Drug Des 2000; 15:431-39.

Sandalova T, Zhong L, Lindqvist Y, Holmgren A, Schneider G. Three-dimensional structure of a mammalian thioredoxin reductase: Implications for mechanism and evolution of a selenocysteine-dependent enzyme. Proc Natl Acad Sci USA 2001; 98:9533-38.

Sarma G N, Savvides S N, Becker K, Schirmer M, Schirmer R H & Karplus P A. Glutathione reductase of the malarial parasite *Plasmodium falciparum*: Crystal structure and inhibitor development. J Mol Biol 2003; 308: 893-907.

Sauthier, M., Leca, F., Toupet, L., Réau, R. Palladium Complexes of a novel family of P,N-chelates, the 2-(2-pyridyl) phospholes: synthesis, structural characterization, and catalytic activity for olefin/CO copolymerization. Organometallics, 2002, 21, 1591-1602.

Savvides S N, Scheiwein M, Boehme C C, Arteel G E, Karplus P A, Becker K & Schirmer R H. Crystal structure of the antioxidant enzyme glutathione reductase inactivated by peroxynitrite. J Biol Chem 2002; 277: 2779-2784.

Smith A D, Guidry C A, Morris V C, Levander O A. Aurothioglucose inhibits murine thioredoxin reductase activity in vivo. J Nutr 1999; 129:194-98.

Soini Y, Kahlos K, Napankangas U, Kaarteenaho-Wiik R, Saily M, Koistinen P, Paakko P, Holmgren A, Kinnula V L. Widespread expression of thioredoxin and thioredoxin reductase in non-small cell lung carcinoma. Clin Cancer Res 2001; 7:1750-57.

Tamura T, Stadtman T C. A new selenoprotein from human lung adenocarcinoma cells: purification, properties, and thioredoxin reductase activity. Proc Natl Acad Sci USA 1996; 93:1006-11.

Welsh S J, Bellamy W T, Briehl M M, Powis G. The redox protein thioredoxin-1 (Trx-1) increases hypoxia-inducible factor 1alpha protein expression: Trx-1 overexpression results in increased vascular endothelial growth factor production and enhanced tumor angiogenesis. Cancer Res 2002; 62:5089-95.

Williams C H J. Lipoamide dehydrogenase, glutathione reductase, thioredoxin reductase, and mercuric ion reductase—a family of flavoenzyme transhydrogenases. In: Müller F, ed. Chemistry and biochemistry of flavoenzymes. Vol. 3. Boca Raton: CRC Press, 1992:121-211.

Wipf P, Hopkins T D, Jung J K, Rodriguez S, Birmingham A, Southwick E C, Lazo J S, Powis G. New inhibitors of the thioredoxin-thioredoxin reductase system based on a naphtoquinone spiroketal natural product lead. Bioorg Med Chem Lett 2001; 11:2637-41.

Xia L, Nordman T, Olsson J M, Damdimopoulos A, Bjorkhem-Bergman L, Nalvarte I, Eriksson L C, Arner E S, Spyrou G, Bjornstedt M. The mammalian cytosolic selenoenzyme thioredoxin reductase reduces ubiquinone. A novel mechanism for defense against oxidative stress. J Biol Chem 2003; 278:2141-46.

Zhao R, Holmgren A. A novel antioxidant mechanism of ebselen involving ebselen diselenide, a substrate of mammalian thioredoxin and thioredoxin reductase. J Biol Chem 2002; 277:39456-62.

Zhao R, Masayasu H, Holmgren A. Ebselen: a substrate for human thioredoxin reductase strongly stimulating its hydroperoxide reductase activity and a superfast thioredoxin oxidant. Proc Natl Acad Sci USA 2002; 99:8579-84.

Zhong L, Arner E S, Holmgren A. Structure and mechanism of mammalian thioredoxin reductase: the active site is a redox-active selenolthiol/selenenylsulfide formed from the conserved cysteine-selenocysteine sequence. Proc Natl Acad Sci USA 2000; 97:5854-59.

Zhong L, Arnér E S, Ljung J, Aslund F, Holmgren A. Rat and calf thioredoxin reductase are homologous to glutathione reductase with a carboxyl-terminal elongation containing a conserved catalytically active penultimate selenocysteine residue. J Biol Chem 1998; 273:8581-91.

Zhong L, Holmgren A. Mammalian thioredoxin reductases as hydroperoxide reductases. Methods Enzymol 2002; 347: 236-43.

The invention claimed is:

1. A pharmaceutical composition, comprising as active ingredient at least one compound of general formula (I) below:

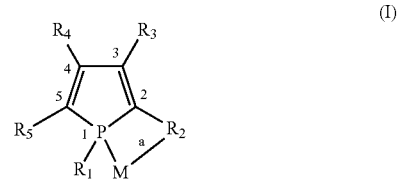

in which:
a is a single bond or no bond,
$R_1$ is a
linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, a linear or branched alkyl group with 1 to 6 carbon atoms, optionally substituted by one or more halogen atoms, or an aryl group with 6 to 14 carbon atoms;
$R_2$ is a nitrogen-containing heteroaryl group or a nitrogen-containing heterocycle with 5 or 6 atoms having from 1 to 4 nitrogen atoms;
$R_3$ and $R_4$ are, independently of one another, a hydrogen atom, or a
linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, a linear or branched alkyl group with 1 to 6 carbon atoms, optionally substituted by one or more halogen atoms, or an aryl group with 6 to 14 carbon atoms, optionally an alkyl group can bridge the carbon atoms in positions 3 and 4 of the phosphole ring carrying, respectively, the substituents $R_3$ and $R_4$, so as to form a ring with 3 to 8 carbon atoms;
$R_5$ is a hydrogen atom, a heterocycle with five or six members having from 1 to 4 nitrogen or sulphur atoms, or a
linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, a linear or branched alkyl group with 1 to 6 carbon atoms, optionally substituted by one or more halogen atoms, or an aryl group with 6 to 14 carbon atoms;
M is a metal atom, optionally carrying from 1 to 2 substituents, $R_6$ and $R_7$, identical or different, which substituents are chosen from
a halogen atom,
a thio-osidic group with 3 to 60 carbon atoms, optionally substituted by one or more groups, identical or different, chosen from the protective groups of the hydroxyl or amine groups, chosen from an alkanoyl group with 2 to 6 carbon atoms, or an arylcarbonyl group with 6 to 14 carbon atoms,
a peptide group comprising from 1 to 5 amino acids, at least one of the amino acids comprising a thio group, chosen from S-cysteine or S-glutathione, or
a linear or branched thioalkyl group with 1 to 6 carbon atoms, a saturated or unsaturated thiocycloalkyl group with 3 to 7 carbon atoms or a thioaryl or thioheteroaryl group with 6 to 14 carbon atoms, optionally substituted by one or more groups, identical or different, chosen from a halogen atom, an alkyl group with 1 to 6 carbon atoms, optionally substituted by one or more halogen atoms, or an aryl group with 6 to 14 carbon atoms;
in combination with a pharmaceutically acceptable vehicle.

2. A pharmaceutical composition, comprising as active ingredient at least one compound of general formula (I) below:

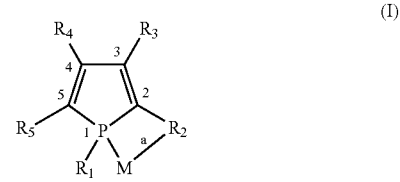

(I)

in which:
a is a single bond or no bond,
$R_1$ is a
linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, a linear or branched alkyl group with 1 to 6 carbon atoms, optionally substituted by one or more halogen atoms, or an aryl group with 6 to 14 carbon atoms;
$R_2$ is a nitrogen-containing heteroaryl group or a nitrogen-containing heterocycle with 5 or 6 atoms having from 1 to 4 nitrogen atoms;

R3 and R4 represent, independently of one another, a hydrogen atom, or a linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, a linear or branched alkyl group with 1 to 6 carbon atoms, optionally substituted by one or more halogen atoms, or an aryl group with 6 to 14 carbon atoms, optionally an alkyl group can bridge the carbon atoms in positions 3 and 4 of the phosphole ring carrying, respectively, the substituents $R_3$ and $R_4$, so as to form a ring with 3 to 8 carbon atoms;

$R_5$ is a hydrogen atom, a heterocycle with five or six members having from 1 to 4 nitrogen or sulphur atoms, or a linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, a linear or branched alkyl group with 1 to 6 carbon atoms, optionally substituted by one or more halogen atoms, or an aryl group with 6 to 14 carbon atoms;

M is a metal atom, optionally carrying from 1 to 2 substituents, $R_6$ and $R_7$, identical or different, which substituents are chosen from
a halogen atom,
a thio-osidic group with 3 to 60 carbon atoms, optionally substituted by one or more groups, identical or different, chosen from the protective groups of the hydroxyl or amine groups, an alkanoyl group with 2 to 6 carbon atoms, or an arylcarbonyl group with 6 to 14 carbon atoms, or
a peptide group comprising from 1 to 5 amino acids, at least one of the amino acids comprising a thio group, chosen from S-cysteine or S-glutathione, or
a linear or branched thioalkyl group with 1 to 6 carbon atoms, a saturated or unsaturated thiocycloalkyl group with 3 to 7 carbon atoms or a thioaryl or thioheteroaryl group with 6 to 14 carbon atoms, optionally substituted by one or more groups, identical or different, chosen from a halogen atom, an alkyl group with 1 to 6 carbon atoms, optionally substituted by one or more halogen atoms, or an aryl group with 6 to 14 carbon atoms;

in combination with a pharmaceutically acceptable vehicle.

3. The pharmaceutical composition according to claim 1, comprising as active ingredient at least one compound of general formula (II) below:

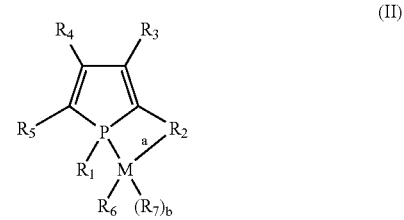

(II)

in which:
a is a single bond or no bond,
b is 0 or 1,
$R_1$, $R_2$, $R_3$, $R_4$ and $R_5$ are as previously defined,
$R_6$ and $R_7$ are, independently of one another,
a halogen atom,
a thio-osidic group with 3 to 60 carbon atoms, optionally substituted by one or more groups, identical or different, chosen from the protective groups of the hydroxyl or amine groups, an alkanoyl group with 2 to 6 carbon atoms, or an arylcarbonyl group with 6 to 14 carbon atoms, or
a peptide group comprising from 1 to 5 amino acids, at least one of the amino acids comprising a thio group, chosen from S-cysteine or S-glutathione, or
a linear or branched thioalkyl group with 1 to 6 carbon atoms, a saturated or unsaturated thiocycloalkyl group with 3 to 7 carbon atoms or a thioaryl or thioheteroaryl group with 6 to 14 carbon atoms, optionally substituted by one or more groups, identical or different, chosen from a halogen atom, an alkyl group with 1 to 6 carbon atoms, optionally substituted by one or more halogen atoms, or an aryl group with 6 to 14 carbon atoms;

M is a divalent, trivalent or tetravalent metal atom, providing that when M is a divalent metal atom then a is no bond and b is 0, when M is a trivalent metal atom then a is no bond and b is 1 and that when M is a tetravalent metal atom then a is a single bond and b is 1.

4. The pharmaceutical composition according to claim 1, comprising as active ingredient at least one compound of general formula (III):

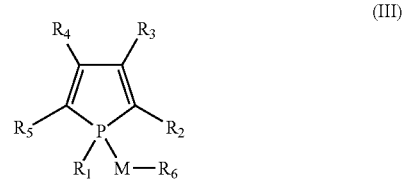

(III)

in which $R_1$, $R_2$, $R_3$, $R_4$, $R_5$ and $R_6$ are as previously defined, and M is a divalent metal atom.

5. The pharmaceutical composition according to claim 1, comprising as active ingredient at least one compound of general formula (IV) below:

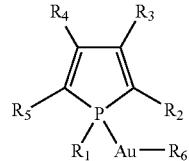

(IV)

in which $R_2$, $R_3$, $R_4$, $R_5$ and $R_6$ are as previously defined.

6. The pharmaceutical composition according to claim 1, comprising as active ingredient at least one compound of general formula (IV') below:

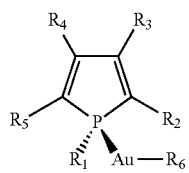

(IV')

in which $R_2$, $R_3$, $R_4$, $R_5$ and $R_6$ are as previously defined.

7. The pharmaceutical composition according to claim 1, comprising as active ingredient at least one compound of general formula (V):

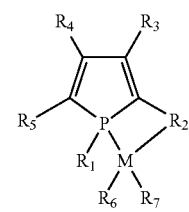

(V)

in which $R_1$, $R_2$, $R_3$, $R_4$, $R_5$, $R_6$ and $R_7$ are as previously defined, and M is a tetravalent metal atom.

8. The pharmaceutical composition according to claim 7, comprising as active ingredient at least one compound of general formula (VI) below:

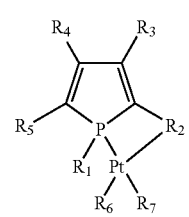

(VI)

in which $R_2$, $R_3$, $R_4$, $R_5$ and $R_6$ are as previously defined.

9. The pharmaceutical composition according to claim 7, comprising as active ingredient at least one compound of general formula (VI') below:

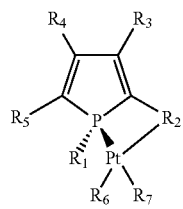

(VI')

in which $R_2$, $R_3$, $R_4$, $R_5$ and $R_6$ are as previously defined.

10. The pharmaceutical composition according to claim 7, comprising as active ingredient at least one compound of general formula (VII) below:

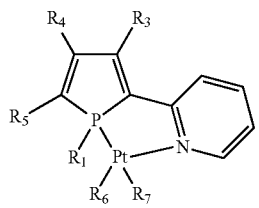

(VII)

in which $R_1$, $R_3$, $R_4$, $R_5$, $R_6$ and $R_7$ are as previously defined.

11. The pharmaceutical composition according to claim 7, comprising as active ingredient at least one compound of general formula (VII') below:

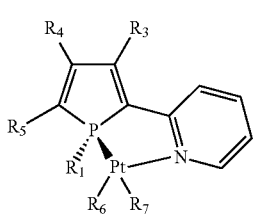

(VII')

in which $R_1$, $R_3$, $R_4$, $R_5$, $R_6$ and $R_7$ are as previously defined.

12. The pharmaceutical composition according to claim 1, wherein:
  $R_1$ is a saturated or unsaturated cycloalkyl group with 3 to 7 carbon atoms or an aryl group with 6 to 14 carbon atoms;
  $R_2$ is a nitrogen-containing heteroaryl group with six atoms having from 1 to 3 nitrogen atoms;
  $R_3$ and $R_4$ are independently of one another an alkyl group with 1 to 6 carbon atoms, and an alkyl group with 3 or 4 carbon atoms linking the atoms in positions 3 and 4 of the phosphole ring;
  $R_5$ is an aryl group with 6 to 14 carbon atoms, a thienyl group with 6 to 14 carbon atoms, or a pyridyl group with 6 to 14 carbon atoms, substituted or non-substituted;
  M is a metal atom;
  $R_6$ and optionally $R_7$ are independently of one another a halogen, a thio-monosaccharide chosen from a thiopentose or a thiohexose, or a thio-disaccharide, optionally substituted by one or more protective groups of the hydroxyl or amine groups chosen from the group consisting of thioglucose, thioglucose tetraacetate, thiomannose, thiomannose tetraacetate, thiogalactose, thiogalactose tetraacetate, thioribose, thioribose triacetate, thioxylose, thioxylose triacetate, thio-allose, thio-allose tetraacetate, thiotalose, thiotalose tetraacetate, thiofucose, thiofucose tetraacetate, thio-N-acetyl-glucosamine, thio-N-acetyl-galactosamine triacetate, thio-N-acetyl-galactosamine, thio-N-acetyl-galactosamine triacetate, thio-N-acetyl mannosamine, thio-N-acetyl mannosamine triacetate, thiolactose, thiolactose heptaacetate.

13. The pharmaceutical composition according to claim 7, comprising as active ingredient at least one compound of the following formula:

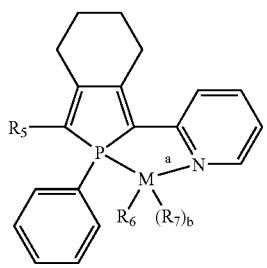

in which $R_5$ is a 2-thienyl or 2-pyridyl group, M is Au or Pt, a is a single bond when M is Pt or no bond when M is Au, b is 1 when M is Pt and 0 when M is Au, and $R_6$ and $R_7$ are as previously defined.

14. The pharmaceutical composition according to claim 13, comprising as active ingredient at least one compound of the following formula:

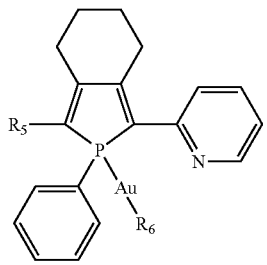

in which $R_5$ is a 2-thienyl or 2-pyridyl group and $R_6$ is as previously defined.

15. The pharmaceutical composition according to claim 1, comprising as active ingredient at least one compound of the following formula:

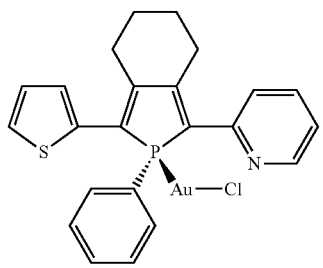

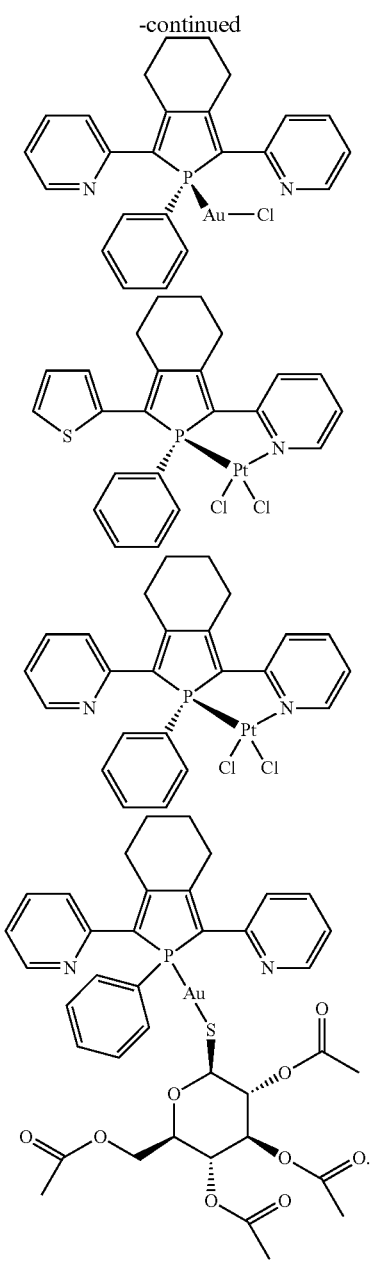

16. The pharmaceutical composition according to claim 1, comprising as active ingredient at least one compound of general formula (I), in combination with at least one anticancer compound chosen from the group consisting of cisplatin, mitomycin C, doxorubicin, etoposide, carmustine.

17. A composition comprising:
at least one compound of general formula (I), as defined in claim 1, in combination with
at least one anticancer compound chosen from the group consisting of cisplatin, mitomycin C, doxorubicin, etoposide, carmustine, for simultaneous or separate use, or use spread over time, in cancer therapy.

18. The composition according to claim 17, comprising at least one compound of general formula (I) and an anticancer agent in a ratio of approximately 0.1/1 to approximately 2.5/1 and optionally, one or more pharmaceutically acceptable vehicles.

19. The pharmaceutical compositions according to claim 1, in a form which can be administered by intravenous route.

20. The pharmaceutical compositions according to claim 1, wherein the dosage of the compounds of formula (I) contained in these pharmaceutical compositions is approximately 5-200 mg/m²/dose.

21. A compound of general formula (IX) below:

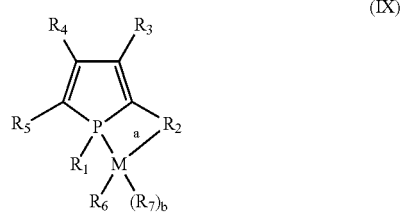

in which:
a is a single bond or no bond,
b is 0 or 1,
$R_1$ is a
linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, a linear or branched alkyl group with 1 to 6 carbon atoms, optionally substituted by one or more halogen atoms, or an aryl group with 6 to 14 carbon atoms;

$R_2$ is a nitrogen-containing heteroaryl group or a nitrogen-containing heterocycle with 5 or 6 atoms having from 1 to 4 nitrogen atoms;

$R_3$ and $R_4$ represent, independently of one another, a hydrogen atom, or a linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, a linear or branched alkyl group with 1 to 6 carbon atoms, optionally substituted by one or more halogen atoms, or an aryl group with 6 to 14 carbon atoms, optionally an alkyl group can bridge the carbon atoms in positions 3 and 4 of the phosphole ring carrying, respectively, the substituents $R_3$ and $R_4$, so as to form a ring with 3 to 8 carbon atoms;

$R_5$ is a hydrogen atom, a heterocycle with five or six members having from 1 to 4 nitrogen or sulphur atoms, or a
linear or branched alkyl group with 1 to 6 carbon atoms,
saturated or unsaturated cycloalkyl group with 3 to 7 carbon atoms,
aryl group with 6 to 14 carbon atoms,
linear or branched alkoxy group with 1 to 6 carbon atoms,
saturated or unsaturated cycloalkoxy group with 3 to 7 carbon atoms,
aryloxy group with 6 to 14 carbon atoms,
linear or branched alkylthio group with 1 to 6 carbon atoms,
saturated or unsaturated cycloalkylthio group with 3 to 7 carbon atoms, or
arylthio group with 6 to 14 carbon atoms,
optionally substituted by one or more groups, identical or different, chosen from a halogen atom, a linear or branched alkyl group with 1 to 6 carbon atoms, optionally substituted by one or more halogen atoms, or an aryl group with 6 to 14 carbon atoms;

M is a divalent, trivalent or tetravalent metal atom, providing that when M is a divalent metal atom then a is no bond and b is 0, when M is a trivalent metal atom then a is no bond and b is 1 and that when M is a tetravalent metal atom then a is a single bond and b is 1, $R_6$ is a thio-osidic group with 3 to 60 carbon atoms, optionally substituted by one or more groups, identical or different, chosen from the protective groups of the hydroxyl or amine groups, an alkanoyl group with 2 to 6 carbon atoms, or an arylcarbonyl group with 6 to 14 carbon atoms, $R_7$ is
a halogen atom,
a thio-osidic group with 3 to 60 carbon atoms, optionally substituted by one or more groups, identical or different, chosen from the protective groups of the hydroxyl or amine groups, an alkanoyl group with 2 to 6 carbon atoms, or an arylcarbonyl group with 6 to 14 carbon atoms,
a peptide group comprising from 1 to 5 amino acids, at least one of the amino acids comprising a thio group, chosen from S-cysteine or S-glutathione, or
a linear or branched thioalkyl group with 1 to 6 carbon atoms, a saturated or unsaturated thiocycloalkyl group with 3 to 7 carbon atoms or a thioaryl or thio-heteroaryl group with 6 to 14 carbon atoms, optionally substituted by one or more groups, identical or different, chosen from a halogen atom, an alkyl group with 1 to 6 carbon atoms, optionally substituted by one or more halogen atoms, or an aryl group with 6 to 14 carbon atoms.

22. The compound according to claim 21, of general formula (X):

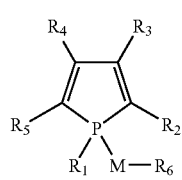

in which $R_1$, $R_2$, $R_3$, $R_4$, $R_5$ and $R_6$ are as previously defined, and M is a divalent metal atom.

23. The compound according to claim 21, of general formula (XI):

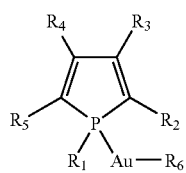

in which $R_2$, $R_3$, $R_4$, $R_5$ and $R_6$ are as previously defined.

24. The compound according to claim 21, in which:
$R_1$ is a cycloalkyl group with 3 to 7 carbon atoms or an aryl group with 6 to 14 carbon atoms;
$R_2$ is a nitrogen-containing heteroaryl group with six atoms having from 1 to 3 nitrogen atoms;
$R_3$ and $R_4$ are independently of one another an alkyl group with 1 to 6 carbon atoms, and an alkyl group with 3 or 4 carbon atoms linking the atoms in positions 3 and 4 of the phosphole ring;
$R_5$ is an aryl group with 6 to 14 carbon atoms, a thienyl group with 6 to 14 carbon atoms, or a pyridyl group with 6 to 14 carbon atoms, substituted or non-substituted;
$R_6$ is a thio-monosaccharide, chosen from a thiopentose or a thiohexose, or a thio-disaccharide, optionally substituted by one or more protective groups of the hydroxyl or amine groups, chosen from the group consisting of thioglucose, thioglucose tetraacetate, thiomannose, thiomannose tetraacetate, thiogalactose, thiogalactose tetraacetate, thioribose, thioribose triacetate, thioxylose, thioxylose triacetate, thio-allose, thio-allose tetraacetate, thiotalose, thiotalose tetraacetate, thiofucose, thiofucose tetraacetate, thio-N-acetyl-glucosamine, thio-N-acetyl-glucosamine triacetate, thio-N-acetyl-galactosamine, thio-N-acetyl-galactosamine triacetate, thio-N-acetyl mannosamine, thio-N-acetyl mannosamine triacetate, thiolactose, thiolactose hepta-acetate;
optionally, $R_7$ is a halogen, a thio-monosaccharide, in particular chosen from a thiopentose or a thiohexose, or a thiodioside, optionally substituted by one or more protective groups of the hydroxyl or amine groups, chosen from the group consisting of thioglucose, thioglucose tetraacetate, thiomannose, thiomannose tetraacetate, thiogalactose, thiogalactose tetraacetate, thioribose, thioribose triacetate, thioxylose, thioxylose triacetate, thio-allose, thio-allose tetraacetate, thiotalose, thiotalose tetraacetate, thiofucose, thiofucose tetraacetate, thio-N-acetyl-glucosamine, thio-N-acetyl-glucosamine triacetate, thio-N-acetyl-galactosamine, thio-N-acetyl-galactosamine triacetate, thio-N-acetyl mannosamine, thio-N-acetyl mannosamine triacetate, thiolactose, thiolactose hepta-acetate.

25. The compound according to claim 24, of the following formula:

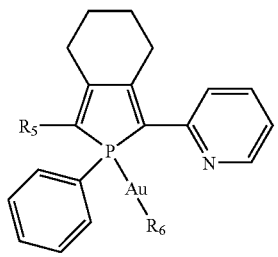

in which $R_5$ and $R_6$ are as previously defined.

26. The compound according to claim 21, of the following formula:

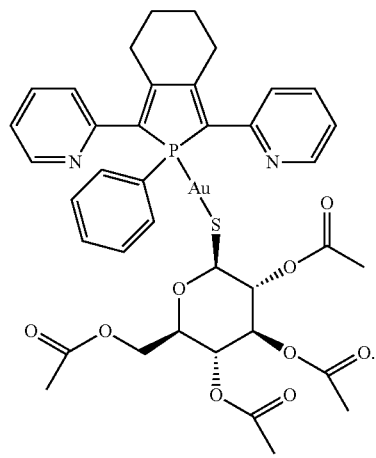

* * * * *